United States Patent
Swager et al.

(10) Patent No.: US 9,995,719 B2
(45) Date of Patent: Jun. 12, 2018

(54) METHODS AND DEVICES FOR SELECTIVE DEPOSITION OF MATERIALS INCLUDING MECHANICAL ABRASION

(71) Applicant: Massachusetts Institute of Technology, Cambridge, MA (US)

(72) Inventors: Timothy M. Swager, Newton, MA (US); Kelvin Mitchell Frazier, Savannah, GA (US); Katherine A. Mirica, Waltham, MA (US); Joseph Walish, West Roxbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 14/831,679

(22) Filed: Aug. 20, 2015

(65) Prior Publication Data
US 2016/0195504 A1 Jul. 7, 2016

Related U.S. Application Data

(60) Provisional application No. 62/039,787, filed on Aug. 20, 2014.

(51) Int. Cl.
*H01L 21/00* (2006.01)
*G01N 33/00* (2006.01)
*B81C 1/00* (2006.01)

(52) U.S. Cl.
CPC ..... *G01N 33/0009* (2013.01); *B81C 1/00031* (2013.01); *B81C 1/00373* (2013.01)

(58) Field of Classification Search
CPC ............................. G01N 27/12; G01N 33/00
USPC ......... 422/82.02; 29/592.1; 438/49; 257/414
See application file for complete search history.

(56) References Cited

U.S. PATENT DOCUMENTS

| 4,889,961 A | 12/1989 | Carlson |
| 6,797,428 B1 | 9/2004 | Skotheim et al. |
| 8,456,073 B2 | 6/2013 | Swager et al. |
| 9,459,222 B2 * | 10/2016 | Swager ................. G01N 27/12 |

(Continued)

FOREIGN PATENT DOCUMENTS

| WO | WO 2008/089787 A1 | 7/2008 |
| WO | WO 2008/133779 A2 | 11/2008 |

(Continued)

OTHER PUBLICATIONS

T. Alvarez., "Abrasion as a Catalyst Deposition Technique for Carbon Nanotube Growth", Department of Chemistry, Department of Physics and Astronomy, Department of Mechanical Engineering and Materials Science, J. Am. Chem. Soc. 2009, 131, 15041-15048.*

(Continued)

*Primary Examiner* — Caleb Henry
(74) *Attorney, Agent, or Firm* — Wolf, Greenfield & Sacks, P.C.

(57) ABSTRACT

Methods for depositing materials on patterned substrates, and related devices, are generally provided. In some embodiments, a material is deposited on a patterned substrate. In certain embodiments, the substrate comprises a first portion with a material deposited on the first portion and a second portion of the substrate essentially free of the material. The methods described herein may be useful in fabricating sensors, circuits, tags, among other devices. In some cases, devices for determining analytes are also provided.

21 Claims, 30 Drawing Sheets

(56) References Cited

U.S. PATENT DOCUMENTS

| | | | |
|---|---|---|---|
| 2008/0035481 | A1 | 2/2008 | McCormack et al. |
| 2010/0173422 | A1* | 7/2010 | Koley .......... G01N 29/022 436/149 |
| 2011/0089051 | A1 | 4/2011 | Wang et al. |
| 2013/0330231 | A1* | 12/2013 | Swager .......... G01N 27/12 422/82.02 |

FOREIGN PATENT DOCUMENTS

| | | | |
|---|---|---|---|
| WO | WO 2009/136978 | A2 | 11/2009 |
| WO | WO 2010/123482 | A2 | 10/2010 |
| WO | WO 2011/055039 | A1 | 5/2011 |
| WO | WO 2011/056936 | A2 | 5/2011 |
| WO | WO 2012/044778 | A1 | 4/2012 |
| WO | WO 2012/050714 | A2 | 4/2012 |
| WO | WO 2012/067665 | A1 | 5/2012 |

OTHER PUBLICATIONS

International Search Report and Written Opinion for Application No. PCT/US2015/046133 dated Nov. 20, 2015.
International Search Report and Written Opinion for Application No. PCT/US2013/030846 dated Nov. 8, 2013.
Albrecht et al., Ultrahigh-vacuum scanning tunneling microscopy and spectroscopy of single-walled carbon nanotubes on hydrogen-passivated Si(100) surfaces. Appl Phys Lett. Dec. 15, 2003;83(24):5029-31.
Ammu et al., Flexible, all-organic chemiresistor for detecting chemically aggressive vapors. J Am Chem Soc. Mar. 14, 2012;134(10):4553-6. Epub Mar. 1, 2012.
Aragay et al., Rapid and highly sensitive detection of mercury ions using a fluorescence-based paper test strip with an N-alkylaminopyrazole ligand as a receptor. J. Mater. Chem. 2012;22(13):5978-83.
Bahr et al., Covalent chemistry of single-walled carbon nanotubes. Journal of Mater Chem. 2002;12:1952-8.
Barr et al., Direct monolithic integration of organic photovoltaic circuits on unmodified paper. Adv Mater. Aug. 16, 2011;23(31):3500-3505. Epub Jul. 8, 2011.
Bekyarova et al., Chemically functionalized single-walled carbon nanotubes as ammonia sensors. J Phys Chem B. 2004;108(51):19717-20.
Britz et al., Noncovalent interactions of molecules with single walled carbon nanotubes. Chem Soc Rev. Jul. 2006;35(7):637-59. Epub Mar. 23, 2006.
Dossi et al., Pencil-drawn paper supported electrodes as simple electrochemical detectors for paper-based fluidic devices. Electrophoresis. Jul. 2013;34(14):2085-91. doi: 10.1002/elps.201200425.
Esser et al., Selective detection of ethylene gas using carbon nanotube-based devices: utility in determination of fruit ripeness. Angew Chem Int Ed Engl. Jun. 4, 2012;51(23):5752-6. Epub Apr. 19, 2012.
Gimenez et al., ZnO-Paper Based Photoconductive UV Sensor. J. Phys. Chem. 2011;115(1):282-87.
Kauffman et al., Carbon nanotube gas and vapor sensors. Angew Chem Int Ed Engl. 2008;47(35):6550-70.
Kong et al., Nanotube molecular wires as chemical sensors. Science. Jan. 28, 2000;287(5453):622-5.
Kurra et al., Pencil-on-paper: electronic devices. Lab Chip. Aug. 7, 2013;13(15):2866-73. doi: 10.1039/c3lc50406a.
Kurra et al., Field effect transistors and RC filters from pencil-trace on paper. Phys Chem Chem Phys. Jun. 7, 2013;15(21):8367-72. doi: 10.1039/c3cp50675d.
Li et al., Carbon nanotube sensors for gas and organic vapor detection. Nano Letters. Jun. 13, 2003;3(7):929-33.
Lin et al., Pencil drawn strain gauges and chemiresistors on paper. Sci Rep. Jan. 22, 2014;4:3812. doi: 10.1038/srep03812.

Lobez et al., Radiation detection: resistivity responses in functional poly(olefin sulfone)/carbon nanotube composites. Angew Chem Int Ed Engl. 2010;49(1):95-8. doi: 10.1002/anie.200904936.
Martinez et al., Diagnostics for the developing world: microfluidic paper-based analytical devices. Anal Chem. Jan. 1, 2010;82(1):3-10.
Martinez et al., Patterned paper as a platform for inexpensive, low-volume, portable bioassays. Angew Chem Int Ed Engl. Feb. 12, 2007;46(8):1318-20.
Martinez et al., Programmable diagnostic devices made from paper and tape. Lab Chip. Oct. 7, 2010;10(19):2499-504. doi: 10.1039/c01c00021c.
Mirica et al., Mechanical drawing of gas sensors on paper. Angew Chem Int Ed Engl. Oct. 22, 2012;51(43):10740-5. Epub Oct. 4, 2012.
Mirica et al., Rapid prototyping of carbon-based chemiresistive gas sensors on paper. Proc Nat Acad Sci. Aug. 13, 2013:E3265-70.
Nery et al., Sensing approaches on paper-based devices: a review. Anal Bioanal Chem. Sep. 2013;405(24):7573-95. doi: 10.1007/s00216-013-6911-4.
Nie et al., Electrochemical sensing in paper-based microfluidic devices. Lab Chip. Feb. 21, 2010;10(4):477-83. Epub Dec. 3, 2009.
Potyrailo et al., Materials and transducers toward selective wireless gas sensing. Chem Rev. Nov. 9, 2011;111(11):7315-54. Epub Sep. 7, 2011.
Röck et al., Electronic nose: current status and future trends. Chem Rev. Feb. 2008;108(2):705-25. Epub Jan. 19, 2008.
Schnorr et al., Emerging applications of carbon nanotubes. Chem Mater. 2011;23:646-57.
Siegel et al., Foldable printed circuit boards on paper substrates. Adv Funct Mater. Jan. 8, 2010;20(1):28-35.
Stitzel et al., Artificial noses. Annu Rev Biomed Eng. Aug. 15, 2011;13:1-25.
Thom et al., "Fluidic batteries" as low-cost sources of power in paper-based microfluidic devices. Lab Chip. Apr. 24, 2012;12(10):1768-70. Epub Mar. 26, 2012.
Tobjörk et al., Paper electronics. Adv Mater. May 3, 2011;23(17):1935-61. Epub Mar. 23, 2011.
UL Hasan et al., Screen Printed ZnO ultraviolet photoconductive sensor on pencil drawn circuitry over paper. Appl. Phys. Lett. 2016;100:211104.
Vyas et al., Inkjet printed, self powered, wireless sensors for environmental, gas, and authentication-base sensing. IEEE Sens J. 2011;11(12):3139-52.
Wang et al., Carbon nanotube/polythiophene chemiresistive sensors for chemical warfare agents. J Am Chem Soc. Apr. 23, 2008;130(16):5392-3. Epub Mar. 29, 2008.
Wang et al., Molecular recognition for high selectivity in carbon nanotube/polythiophene chemiresistors. Angew Chem Int Ed Engl. 2008;47(44):8394-6.
Wang et al., Paper-based three-dimensional electrochemical immunodevice based on multi-walled carbon nanotubes functionalized paper for sensitive point-of-care testing. Biosens Bioelectron. Feb. 15, 2012;32(1):238-43. Epub Dec. 23, 2011.
Wang et al., Simple, rapid, sensitive, and versatile SWNT-paper sensor for environmental toxin detection competitive with ELISA. Nano Lett. Dec. 2009;9(12):4147-52.
Wilson et al., Applications and advances in electronic-nose technologies. Sensors (Basel). 2009;9(7):5099-148. Epub Jun. 29, 2009.
Yao et al., Paper-based solid-state supercapacitors with pencil-drawing graphite/polyaniline networks hybrid electrodes. Nano Energy. Nov. 2013;2(6):1071-8.
Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.
Zhang et al., Modular functionalization of carbon nanotubes and fullerenes. J Am Chem Soc. Jun. 24, 2009;131(24):8446-54.
Zhang et al., Poly(m-aminobenzene sulfonic acid) functionalized single-walled carbon nanotubes based gas sensor. Nanotechnology. Mar. 23, 2007;18(16):156604. 6 pages.

* cited by examiner

*Unmodified substrates*

Adhesive tape    Unpolished Silicon Wafer

*Modified substrates*

PMMA             Weighing Paper

Laser-etched PMMA → Deposition of Sensing Materials (SWCNT-based) → Deposition of Graphite Electrodes

| | Laser-Etched Weighing Paper | | Laser-Etched PMMA | | Adhesive Tape | | Unpolished Silicon Wafer | |
|---|---|---|---|---|---|---|---|---|
| | Distance (cm) | Resistance (kΩ) | Distance (cm) | Resistance (kΩ) | Distance (cm) | Resistance (kΩ) | Distance (cm) | Resistance (kΩ) |
| 1 | 2.2 | 7-8.4 | 2.2 | 2-2.6 | 1.7 | 8-9.9 | 2.2 | 4-4.8 |
| 2 | 2.2 | 5-6.5 | 2.2 | 2-2.5 | 2 | 8-9.7 | 2.2 | 3-3.7 |
| 3 | 0.8 | 2.8-5.5 | 0.8 | 0.8-1.2 | 0.7 | 2.6-3.2 | 0.8 | 2.1-2.4 |
| 4 | 1.3 | 4.2-6.5 | 1.3 | 1.6-2.3 | 0.9 | 2.7-3.2 | 1.3 | 2.7-3.8 |

METHODS AND DEVICES FOR SELECTIVE DEPOSITION OF MATERIALS INCLUDING MECHANICAL ABRASION

RELATED APPLICATIONS

This application claims priority under 35 U.S.C. § 119(e) to U.S. Provisional Application Ser. No. 62/039,787, filed Aug. 20, 2014, which is incorporated herein by reference in its entirety for all purposes.

GOVERNMENT SPONSORSHIP

This invention was made with Government support under Grant Nos. W911NF-14-1-0087 and W911NF-13-D-0001 awarded by the Army Research Office, and Grant No. F32 CA157197 awarded by the National Institutes of Health. The Government has certain rights in the invention.

FIELD OF THE INVENTION

Methods for depositing materials on patterned substrates, and related devices, are generally provided.

BACKGROUND OF THE INVENTION

Chemical sensors that identify and monitor volatile organic compounds (VOCs) have an important role in assessing public security, food and water quality, industrial environment, and health. For example, the detection of residual volatile organic compounds (VOCs) in consumer goods such as food, shelter, clothing, and medicine and to protect workers from occupational exposure is desirable. Presently, monitoring and determination of the chemical components of gas samples is typically performed using expensive gas chromatography-mass spectrometry (GC-MS) which has limited portability and requires highly trained users.

Carbon nanotubes (CNTs), are useful materials in chemical sensing as a result of the sensitivity of their electrical conductance to the presence of chemical analytes. For example, CNTs may be covalently or non-covalently functionalized with polymers, metals, or small molecules to enhance the selectivity and sensitivity of these materials to specific analytes. However, dependence on expensive specialized equipment for the fabrication of devices, the need for solution processing, and requirements for chemical functionalization for achieving specificity have limited the applications and wide applicability of these materials. For example, carbon nanotubes (CNTs) are promising materials for sensing of gases and volatile organic compounds; however, their poor solubility in most solvents has hindered the solution-based process of covalent or non-covalent chemical functionalization of CNTs, and the subsequent integration of these materials into devices. Additionally, methods for fabricating devices with CNTs are often expensive and time-consuming. For example, covalent and non-covalent functionalization of CNTs to generate selective sensing materials in solution often takes hours and sometimes days. Integration of these materials into devices by drop casting, spin coating, and inkjet printing typically requires prolonged drying times to remove solvent, and often involves several repeated processing cycles to obtain devices with desired electrical properties. Furthermore, known methods for fabricating such devices often require the use of toxic solvents, surfactants, or prolonged sonication for dispersing materials in solution.

SUMMARY OF THE INVENTION

Methods for depositing materials on patterned substrates, and related devices, are generally provided.

In one aspect, methods for fabricating a device are provided. In some embodiments, the method comprises providing a substrate comprising a first portion and a second portion, contacting essentially identically the first portion and the second portion of the substrate with an article comprising a first material via mechanical abrasion, thereby forming the first material on the first portion while leaving the second portion essentially free of the first material, or forming the first material on the second portion in an amount at least 10% less per unit area of substrate than the first material formed on the first portion.

In certain embodiments, the method comprises providing a substrate comprising a first portion and a second portion, wherein an average affinity of the first portion to a first material is greater than an average affinity of the second portion to the first material, contacting the first portion and the second portion of the substrate essentially identically with an article comprising the first material via mechanical abrasion.

In some embodiments, the method comprises providing an article comprising a first material, providing a patterned substrate, contacting the article with the patterned substrate via mechanical abrasion, thereby forming the first material on the patterned substrate.

In certain embodiments, the method comprises providing an article comprising a first material, providing a substrate, contacting the article with the substrate via mechanical abrasion, wherein the material is deposited in a pattern directed by the substrate.

In another aspect, a device is provided. In some embodiments, the device comprises a substrate comprising a first portion and a second portion adjacent the first portion, a first material deposited on the first portion, wherein the first portion has a different average affinity for the first material than the second portion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

(FIGS. 2B and 2C) the normalized conductance response of devices exposed to various concentrations of pyridine for 30 seconds with 60 seconds recovery time.

(FIG. 4B) the average normalized conductive response to exposure to various gas analytes for 30 seconds with 60 seconds recovery time; (FIG. 4C) a principal component analysis plot of various gas analytes for the average conductive responses.

(FIG. 7B) normalized average conductive responses of at least three sensors simultaneously exposed four consecutive times to 50 ppm pyridine for 30 s with recovery time of 60 s.

(FIG. 15B) normalized average conductive responses of various sensors upon exposure to 550 ppm pyridine.

(FIG. 16B) normalized average conductive response of three devices simultaneously exposed five consecutive times to various VOCs for 30 s with a recovery time of 60 s.

Figure 1A:
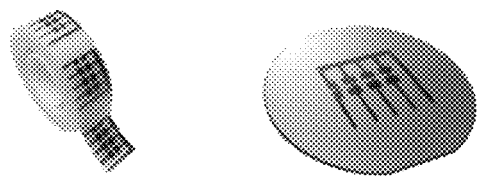
FIGS. 1A-1D show photographs of sensors fabricated by deposition of sensing materials and graphite-based pencil on laser-etched substrates (PMMA and weighing paper) and unmodified substrates (adhesive tape and silicon wafer).

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful in the fabrication of devices including carbon-based materials. Methods and devices described herein may allow for rapid prototyping, fabrication, and screening of devices including various carbon-based materials, and may be useful in fabricating sensors, circuits, tags for remotely-monitored sensors or human/object labeling and tracking, among other devices. Furthermore, methods and devices described herein may allow for parallel fabrication of devices with micro- and nanostructures comprising diverse nanocomposites with precise control over structural features and the location of individual structures.

In some cases, methods described herein may provide the ability to produce a variety of devices unconstrained by the limits of previous methods. In some cases, a wide range of carbon-based material patterns may be formed on a substrate without being limited by the capabilities of printing, dip coating, drop casting, photolithography, or drawing. For example, the location, size, thickness, and/or distribution of deposited carbon-based "films" by previous methods may be difficult to control and may be limited by the features of the substrate (e.g., surface roughness, distribution of cellulose fibers on the surface of paper). In some embodiments, the devices described herein may be fabricated in the absence of solvents (e.g., toxic solvents, surfactants, and the like), eliminating the need for prolonged drying times and/or prolonged sonication times and/or unsafe exposure to toxic solvents that pose a risk to human health or the environment. In certain embodiments, the devices may be fabricated depositing a carbon-based material on a substrate such that the material is deposited in a pattern directed by the substrate.

The resulting devices may be flexible, bendable, and stackable, while maintaining various electrochemical properties (e.g., conductance) when the device is bent, creased, or otherwise physically distorted from its original shape. In some cases, the methods may allow for fabrication of devices having readily tunable electronic properties.

Another advantageous feature provided by devices and methods described herein is the ability to readily incorporate (e.g., process) conductive materials such as carbon nanotubes, as well as other components, into devices. For example, a device may include materials (e.g., carbon nanotubes, graphene, nanostructured graphite, etc.) which might otherwise be difficult to process using previous methods, for example, due to insolubility of the materials and/or complex synthetic procedures needed to fabricate the materials, or the inability to precisely control the structural features and/or location of individual structures. Some embodiments of the invention provide simplified fabrication methods for devices comprising materials such as carbon nanotubes.

Various methods for fabrication of devices are provided. In some cases, the method involves contacting an article (e.g., a solid article) which comprises a material with a surface of a substrate, thereby forming the material on the surface of the substrate. In some embodiments, the article is contacted with the substrate using mechanical abrasion (e.g., physical abrasion). Mechanical abrasion, as used herein, means contact in a manner such that material is transferred from the article to the substrate surface by being physically abraded from the article whereupon at least some material deposits on the substrate surface, or by contacting the substrate with the article in another manner such that at least some of the material is urged from the article to the substrate surface. For example, a surface of the article may be rubbed along the surface of the substrate to deposit the material on the substrate. In some cases, the material may be drawn on the surface of the substrate with the article, either manually or by an automated device. In some embodiments, the material is deposited on only a portion of the substrate contacted by the article.

In some embodiments, the substrate comprises one or more portions (e.g., a first portion and a second portion). In some cases, the method involves contacting (e.g., using mechanical abrasion) an article which comprises a material with a first portion of the substrate and a second portion of the substrate, thereby forming (i.e. deposited) the material on the first portion of the substrate. In some embodiments, the article is contacted essentially identically on the one or more portions of the substrate (e.g., the first portion and the second portion). The phrase contacted essentially identically generally refers to the contact of the article with one or more portions of a substrate at an angle, a force and/or pressure, a speed, a temperature, a humidity, or combinations thereof that do not differ significantly on the one or more portions of the substrate per unit area. That is to say, if the first portion and the second portion of the substrate were identical (i.e. identical chemical composition, identical average surface roughness, identical surface properties), contacting the first portion and the second portion of the substrate with the article would result in the same application of the material in terms of thickness, electrical conductivity, concentration, etc. per unit area of the substrate. For example, contacting a first portion of a substrate and a second portion of a substrate essentially identically with an article comprising a material may result, in some cases wherein the first portion and the second portion of the substrate were identical, in the same amount of material deposited per unit area on the first portion and the second portion of the substrate. In some cases, wherein the first portion of the substrate and the second portion of the substrate are not identical and are contacted essentially identically with an article comprising a material, the material may not be deposited in the same amount per unit area on the first portion and the second portion.

In certain embodiments, the material is not formed (i.e. deposited) on the second portion of the substrate. That is to say, in some cases, the second portion is essentially free of the material. "Essentially free," as used herein, means that the second portion (or another portion essentially free of the material) is not literally free of the material, as a trace number of molecules or material will be present in any area surrounding an abrasion or other deposition event, but that the portion free of the material does not have an amount of the material appreciable in the context of the purpose of the particular deposition. As just one example, if material is deposited on the first portion and a second portion remains essentially free of the material, the material being designed to be electrically conductive, then the first portion will result in enough material for sufficient conductivity for the particular objective, while the second portion will be essentially non-conductive or of a conductivity essentially identical to that of the substrate alone. Other examples will be apparent to those of ordinary skill in the art. In other embodiments, the second portion does not remain essentially free of the material but includes some of the material. For example, some embodiments, the material is formed on the second portion of the substrate in an amount less than the material formed on the first portion of the substrate. For example, the material may be formed on the second portion of the substrate in an amount at least about 10%, at least about 20%, at least about 30%, at least about 50%, at least about 70%, at least about 80%, at least about 90%, at least about 95%, or at least about 99% less per unit area of substrate than the material formed on the first portion of the substrate (e.g., a lower mass of the material may be deposited on the second portion of the substrate than on the first portion of the substrate). In these embodiments the amount of material can be measured readily by those of ordinary skill in the art depending upon the composition of the substrate and composition of the material, for example, via SEM, mapping of particular atoms present and/or absent in the substrate or material (atoms differing between the material and substrate), STM, or the like.

In certain embodiments, a first portion of a substrate may have a greater average affinity for the material than a second portion of the substrate. For example, the first portion of a substrate may have a different texture (roughness), chemical functionalization, different chemical composition, greater average wettability, greater average net charge, or greater Young's elastic modulus than the second portion of the substrate. In some embodiments, differences in affinity may result in differing amounts of material to be deposited on the substrate. For example, a first portion of a substrate may have a greater average wettability than a second portion of the substrate, resulting in more material being deposited on the first portion than the second portion. Those skilled in the art will be capable of selecting appropriate affinities for various materials for use in the methods described herein.

In a subset of embodiments, the different affinities of one or more portions of a substrate are for a carbon-based material. In another subset of embodiments, the different affinities of one or more portions of a substrate are for a conductive material. In yet another subset of embodiments, the different affinities of one or more portions of a substrate are for an insulating material.

In some cases, the first portion of the substrate may have a greater average roughness (e.g., root-mean squared roughness) than the second portion of the substrate. Differences in average roughness may, in some cases, result in different amounts of material to be deposited on the substrate. That is to say, more material may transfer from or be deposited from an article comprising the material when contacting (e.g., rubbing) a first portion of the substrate with a greater average roughness than a second portion of the substrate. In some embodiments, a portion of a substrate may have an average roughness ranging between about 0.1 microns and about 50 microns. In certain embodiments, a portion of a substrate (e.g., a first portion, a second portion) may have an average roughness of at least about 0.1 microns, at least about 0.3 microns, at least about 0.5 microns, at least about 1.0 microns, at least about 2.0 microns, at least about 3.0 microns, at least about 5.0 microns, at least about 8.0 microns, at least about 10 microns, at least about 15 microns, at least about 20 microns, or at least about 30 microns. In some embodiments, a portion of a substrate (e.g., a first portion, a second portion) may have an average roughness of less than or equal to about 50 microns, less than or equal to about 30 microns, less than or equal to about 20 microns, less than or equal to about 15 microns, less than or equal to about 10 microns, less than or equal to about 8 microns, less than or equal to about 5 microns, less than or equal to about 3 microns, less than or equal to about 1 micron, less than or equal to about 0.5 microns, or less than or equal to about 0.3 microns. Combinations of the above-referenced ranges are also possible (e.g., between about 0.1 microns and about 20 microns, between about 0.5 microns and about 5.0 microns, between about 3 microns and about 10 microns).

In some embodiments, differences in an affinity and/or an average roughness of a portion of a substrate may result in a different average thickness of the material deposited on the portion of the substrate. For example, an average thickness of the material deposited on a second portion of a substrate may be at least about 10%, at least about 20%, at least about 30%, at least about 50%, at least about 60%, at least about 80%, at least about 90%, at least about 95%, or at least about 99% less than an average thickness of the material deposited on a first portion of the substrate. For example, the average thickness of the material deposited on a portion of the substrate may range between about 0.1 microns and about 10 microns. Other values for average thickness are also possible. In some embodiments, the average thickness of the material deposited on a portion of the substrate may be at least about 0.1 microns, at least about 0.2 microns, at least about 0.4 microns, at least about 0.5 microns, at least about 1.0 microns, at least about 1.5 microns, at least about 2.5 microns, at least about 4 microns, at least about 5 microns, at least about 7 microns, or at least about 9 microns. In certain embodiments, the average thickness of the material deposited on a portion of the substrate may be less than or equal to about 10 microns, less than or equal to about 9 microns, less than or equal to about 7 microns, less than or equal to about 5 microns, less than or equal to about 4 microns, less than or equal to about 2.5 microns, less than or equal to about 1.5 microns, less than or equal to about 1.0 microns, less than or equal to about 0.5 microns, less than or equal to about 0.4 microns, or less than or equal to about 0.2 microns. Combinations of the above-referenced ranges are also possible (e.g., between about 1.5 microns and about 5 microns, between about 0.1 microns and about 0.4 microns).

In certain embodiments, the material deposited on the substrate is deposited in a pattern directed by the substrate. For example, in some embodiments, the substrate may be patterned. That is to say, the substrate may comprise two or more portions (e.g., having different affinities for the material, having different average roughness) that alternate along one or more directions of the surface. In certain embodiments, the differences in affinities and/or average roughness between two or more portions may be substantially continuous (e.g., a gradient). In some embodiments, the method comprises contacting an article comprising the material with a patterned substrate via mechanical abrasion, thereby forming the material on the patterned substrate.

The substrate may comprise any suitable material. The substrate can comprise a wide variety of materials, as will be appreciated by those in the art, including printed circuit board (PCB) materials. Suitable substrates include, but are not limited to, glass, fiberglass, Teflon, ceramics, metals, glass, diamond, silicon, mica, plastics and polymers of any kind (including acrylics, polystyrene and copolymers of styrene and other materials, polypropylene, polyethylene, polybutylene, polycarbonate, polyurethanes, cellulose acetate, polyethylene terephthalate, polymethyl methacrylate (PMMA), and derivatives thereof, etc.), GETEK (a blend of polypropylene oxide and fiberglass), paper (e.g., weighing paper, or other cellulose-based papers), fabric, skin, wood, plants (e.g., leaves), or combinations thereof, among others. In one set of embodiments, the substrate is paper (e.g., weighing paper). In some embodiments, the substrate comprises glass. In certain embodiments, the substrate comprises PMMA. In some embodiments, the substrate may include a semiconductor material.

The substrate may be modified using any suitable technique. For example, the affinity to a material and/or average roughness of a substrate may be altered by chemical etching, laser etching, scratching, nanoindentation, chemical functionalization and/or modification (e.g., spraying adhesive, lithography), patterning, or combinations thereof. In some embodiments, the method comprises further modifying the substrate to form a third portion of the substrate having an affinity to a material and/or an average roughness that is the same or different from the first and/or second portion of the substrate. In certain embodiments, the third portion is formed after the article comprising a first material is contacted with the substrate. In some embodiments, contacting the third portion with the article comprising a second material results in the deposition of the second material on the third portion. In some cases, the first portion and/or second portion are essentially free of the second material. In some embodiments, the second material is formed on the third portion in an amount less per unit area of substrate than the second material formed on the first portion and/or second portion. For example, the second material is formed on the third portion in an amount at least 10% less per unit area of substrate than the second material formed on the first portion and/or second portion. Other amounts are also possible, as described above. In certain embodiments, the first material and the second material are the same or different.

In some embodiments, one or more materials is deposited on the substrate, as described herein. The ability to deposit one or more materials on a patterned substrate offers several advantages over non-patterned substrates, including precise control over location, thickness, and other structural features of resulting deposited films and/or nanostructures. Those skilled in the art will be capable of selecting suitable materials for use in the devices and methods described herein. Non-limiting examples of suitable materials include carbon-based materials, conductive materials (e.g., conductive polymers, carbon nanotubes), semi-conducting materials, metals, small molecules, polymers, insulating materials. For example, in some cases, the material may be a conductive material capable of conducting charge, including inorganic materials (e.g., metals, alloys, semiconductors), organic materials, organometallic materials, and/or combinations thereof. For example, the conductive material may include nanostructures (e.g., nanotubes, nanoparticles, graphene, etc.), polymers (e.g., conductive polymers), metal-containing species (e.g., metals (e.g., copper), metal salts, etc.), nanoparticles, powders, biological species (e.g., proteins, DNA, RNA, etc.), and/or small molecules. In some cases, the material comprises a carbon-based material. For example, the conductive material may include a nanostructured form of carbon, such as carbon nanotubes, graphite, or graphene. In some embodiments, the material comprises carbon nanotubes, including single-walled carbon nanotubes and/or multi-walled carbon nanotubes. The carbon nanotubes may be provided as a solid, dispersion, suspension, an aligned array, or a randomly-oriented network.

In some embodiments, a first material is deposited on the substrate and a second material is deposited on the first material. In some such embodiments, the first material has a different electron affinity that the second material. For example, the first material may have a higher electron affinity than the second material. In certain embodiments, the first material is a n-type semiconductor and the second material is a p-type semiconductor. Depositing different materials on top of each other can give rise to devices that have a directional conducting property. For example, a diode can be fabricated by depositing a high electron affinity polymer and a lower electron affinity material on the substrate. In some embodiments, the first material and the second material are pure materials (e.g., essentially undoped). In some cases, forming electrical contact to the pure materials and passing current may provide for a different electrical resistance depending upon the direction of the current flow (e.g., diodes). Some embodiments comprise forming an optically responsive device comprising such diodes (e.g., wherein absorption of light causes a photovoltage to be generated between the first and second materials). Such a device could be used to detect light or generate small amounts of power. In some cases, differences in the electrical resistance will occur in response to a chemical or biomolecule bound (e.g., covalently, non-covalently) to the first material and/or second material. For example, the device comprising a second material deposited on the first material may be used as a chemical and/or biological sensor.

The method may further involve forming an electrical circuit that includes the conductive material. In some cases, an electrode material may be arranged to be in electrochemical communication with the conductive material, and a potential may then be applied to the electrode material. "Electrochemical communication," as used herein, refers to materials that are in sufficient communication with each other, such that the transfer of electrons, polarons, excitons, and/or protons can occur between the two materials. For example, the first and second electrodes may not physically contact one another but may be in electrochemical communication with one another via the conductive material, such that upon application of a voltage or potential, a current flows from the one electrode through the conductive material to the other electrode.

In some embodiments, the method may further involve arranging one or more species or "selectors" responsive to an analyte, or analytes, and/or to a change in a set of conditions in the surrounding environment, in electrochemical communication with the conductive material such that, in the presence of the analyte or upon occurrence of the change in the set of conditions, a determinable signal of the device is produced. The signal may, in some cases, provide information relating to the presence, identity, amount, and/or other characteristic of the one or more analytes. In some cases, the signal may indicate a change in the environment in which the device is placed. Signals produced by the device can be monitored and read by various methods, including optical methods, or electric or electrochemical methods using, for example, standard electronic characterization techniques or an RFID reader.

The species (e.g., "selector") may be any moiety that may interact with an analyte and/or that may be responsive to a change in a surrounding medium or environment, and may be incorporated within the device in various configurations. For example, the species may be a small molecule, a polymer, a biological species, or the like. In some embodiments, the species may comprise ionic species (e.g., a salt). In some embodiments, the species may comprise a neutral species. The species may be an organic, organometallic, or an inorganic species. In some cases, the species may be attached to the material (e.g., the conductive material) via a bond. In some cases, the species may be substantially contained within (e.g., dispersed within) the material (e.g., the conductive material), and may not form a covalent bond to the material. In some embodiments, an article containing both the material and the species may be provided, such that contacting the article with the surface of a substrate via mechanical abrasion results in the formation of the material and the species on the surface of the substrate.

In some cases, the mass ratio of the material (e.g., the conductive material) to the species (e.g., selector) is about 1:0, about 1:1, about 1:2, about 1:3, about 1:4, about 1:5, about 1:6, about 1:7, about 1:8, or, in some cases, about 1:9. In certain embodiments, it may be desirable to have a mass ratio of conductive material to species that is about 1:0, about 1:1, about 1:2, or about 1:5).

The interaction between the analyte and the species may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise Van der Waals interactions. In one embodiment, the interaction comprises forming a covalent bond with an analyte. In some cases, the interaction between the device and the analyte may comprise a reaction, such as a charge transfer reaction. In other embodiments, the species and/or another device component may undergo a chemical or physical transformation upon a change in the surrounding environment (e.g., change in temperature) to produce a determinable signal from the device.

In some embodiments, the analyte may contact, or may be positioned in sufficient proximity to, the species, or may permeate an interior portion of the device. In some embodiments, a volumetric or dimensional change (e.g., increase, decrease) of the device may occur upon interaction with an analyte. For example, a component of the device may "swell" upon absorption of the analyte, wherein the change in volume may produce a change in a property of the device.

In some cases, the species may comprise a biological or a chemical group capable of binding another biological or chemical molecule in a medium (e.g., solution, vapor phase, solid phase). For example, the species may include a functional group, such as a thiol, aldehyde, ester, carboxylic acid, hydroxyl, and the like, wherein the functional group forms a bond with the analyte. In some cases, the species may be an electron-rich or electron-poor moiety wherein interaction between the analyte and the species comprises an electrostatic interaction. In some cases, the interaction between the analyte and the species includes binding to a metal or metal-containing moiety.

The species may also interact with an analyte via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA.

In some embodiments, the species may be an aromatic species substituted with one or more halo-containing groups. In one set of embodiments, the species is a fluorine-containing aromatic species. For example, the species may be an aromatic species substituted with one or more fluoro groups, or an aromatic species substituted with a group comprising one or more fluoro groups. In some cases, the fluorine-containing aromatic species is an aromatic species substituted with one or more fluoro groups, fluoroalkyl groups, and/or fluorinated alcohol groups (e.g., hexafluoro-isopropanol). For example, the fluorine-containing aromatic species may be a fluoro-substituted naphthalene. In another example, the fluorine-containing aromatic species may be a naphthalene species substituted with a hydroxyl group and a fluorinated alcohol group. Illustrative embodiments of fluorine-containing aromatic species include

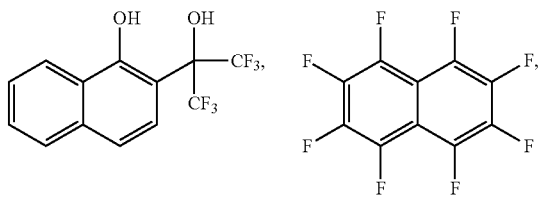 [SMILES: Oc1c(C(O)(C(F)(F)F)C(F)(F)F)ccc2ccccc12 ; Fc1c(F)c(F)c2c(F)c(F)c(F)c(F)c2c1F]

and

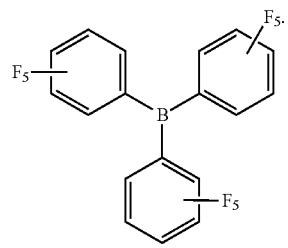

In some embodiments, the species may comprise a fluorinated alcohol group, such as a hexafluoroisoproanol group. In some cases, the species comprising the fluorinated alcohol group is

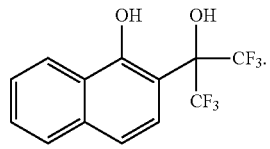 [SMILES: Oc1c(C(O)(C(F)(F)F)C(F)(F)F)ccc2ccccc12]

In some embodiments, the species may be a metal-containing species. For example, the species may be a metal-containing species, including metal salts. In some embodiments, the metal salt is a transition metal salt or complex. Some examples of metal salts include, but are not limited to, $TiO_2$, $TiCl4$, and other titanium salts, AgCl, $AgPF_6$, $Ag(OCOCF_3)$, $Ag(SO_3CF_3)$, and other silver salts, $PtCl_2$ and other platinum salts, $Au_2Cl_6$ and other gold salts, $Al(OEt)_3$ and other aluminum salts, $Ni(SO_3CF_3)_2$, $NiCl_2$, and other nickel salts, and $Cu(SO_3CF_3)$ and other copper salts. In some cases, the species may be a copper-containing species. In some cases, the copper-containing species is a salt, such as a Cu(II) salt. In some cases, the species may be a palladium-containing species. In some cases, the palladium-containing species is a salt, such as a Pd(II) salt. Some examples of specific metal containing species include, but are not limited to,

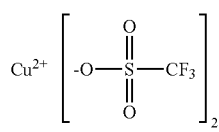

and

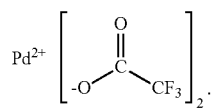

In some embodiments, the species may be a metal complex capable of interacting with ethylene. An example of such a metal complex is described in Esser et al., "Selective Detection of Ethylene Gas Using Carbon Nanotube-based Devices: Utility in Determination of Fruit Ripeness," Angew. Chem. Int. Ed. 2012, 51(23), 5752-5756, the contents of which are incorporated herein by reference in its entirety for all purposes.

In some embodiments, the species may be an optionally substituted polycyclic aromatic group, such naphthalene, phenanthrene, pyrene, anthracene, fluoranthene, perylene, benzopyrene, any of which is optionally substituted, and the like.

In some embodiments, the species may be a quinone-containing species or an oxidized derivative of an aromatic group, including polycyclic aromatic groups. Examples of such species include 1,4-benzoquinones or cyclohexadiene-diones, 1,2-benzoquinones (ortho-quinones), 1,4-naphthoquinones and 9,10-anthraquinones and the like. In one embodiment, the species is 2,3-dichloro-5,6-dicyano-1,4-benzoquinone (DDQ).

Figure 4A:
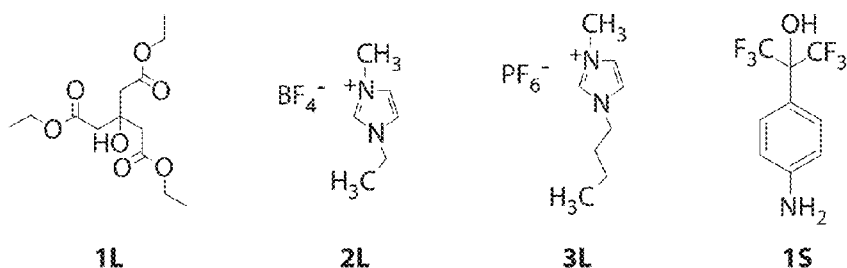
FIGS. 4A-4C shows devices fabricated by mixing SWNCT with various materials, including (FIG. 4A) various liquid and solid selectors.
Figure 4B:
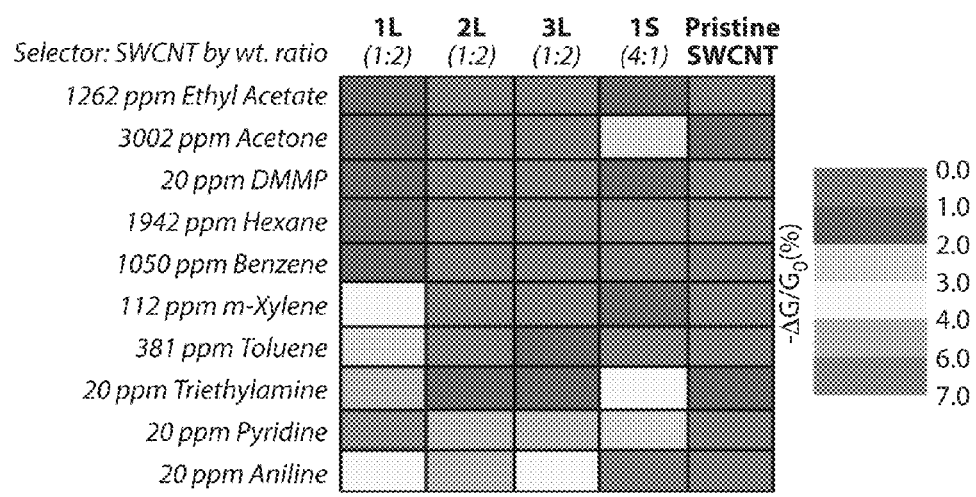
Figure 4C:
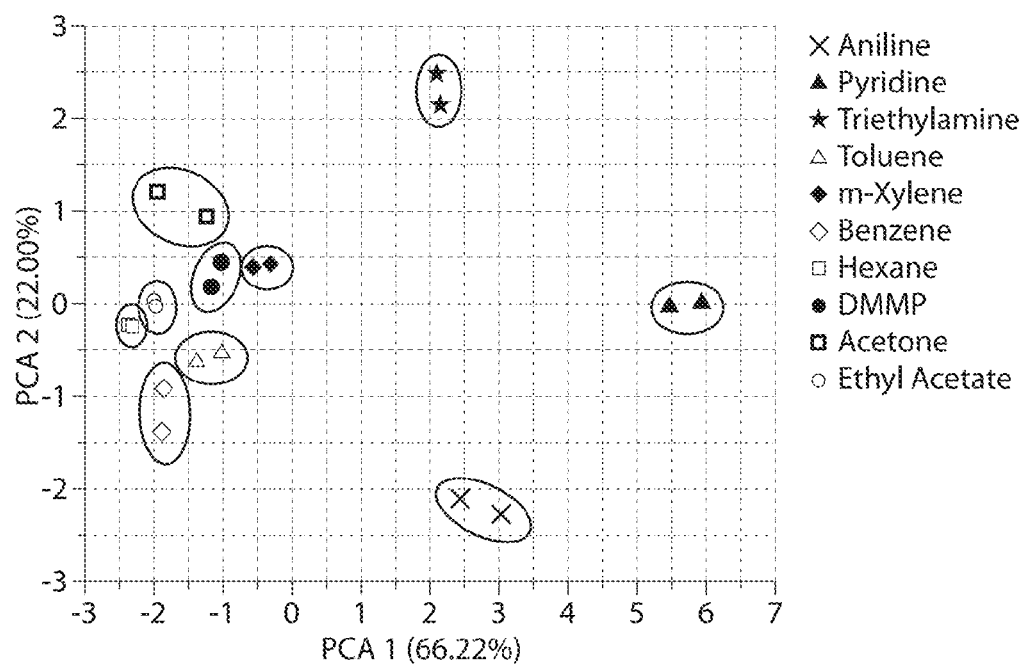
Figure 16A:
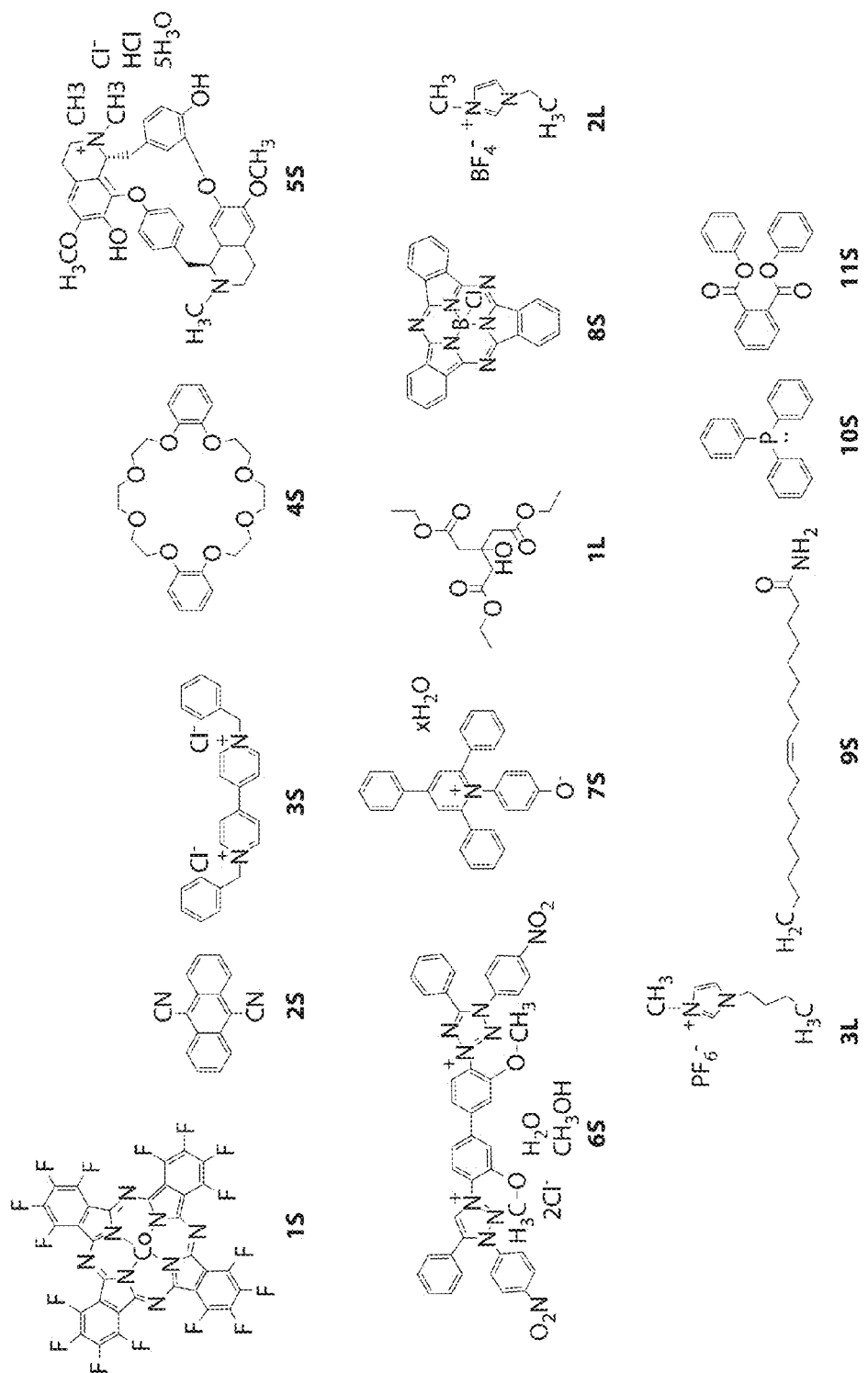
FIGS. 16A-16B shows the sensing responses ($-\Delta G/G_0$, %) of a chemiresistor array fabricated on adhesive tape, including (FIG. 16A) various selectors mixed with SWCNT deposited on top of and between gold electrodes by abrasion onto adhesive tape.
Figure 16B:
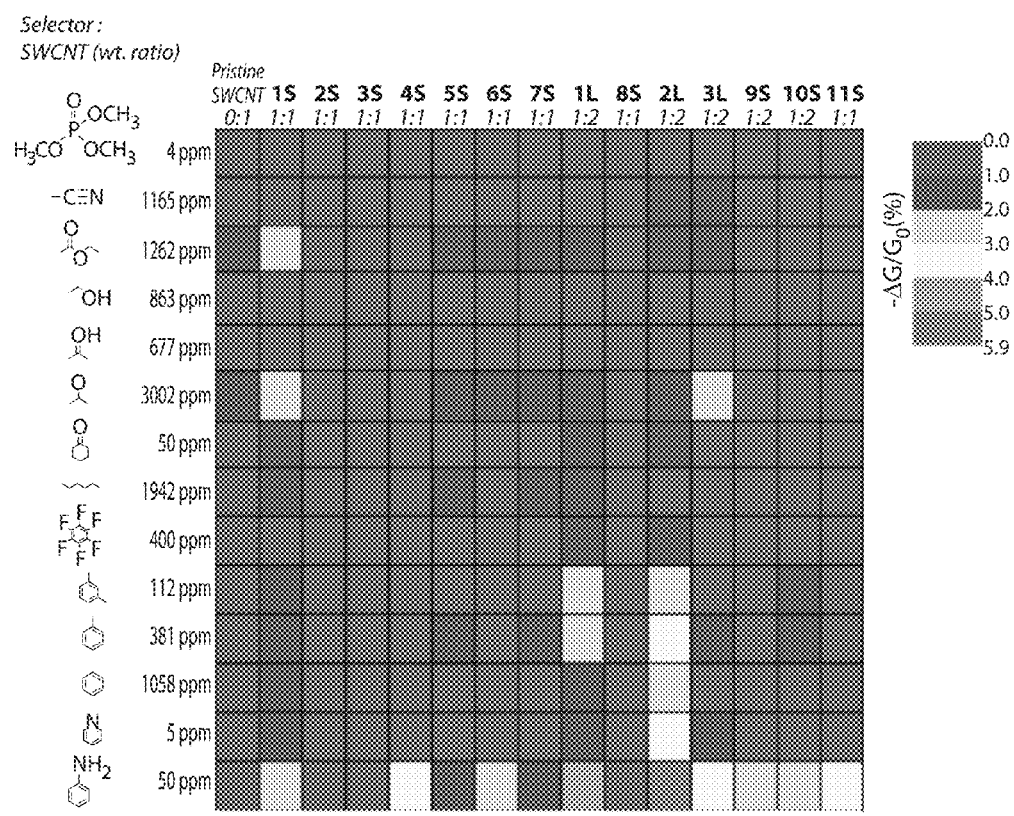

FIG. 4C AND FIG. 16A show examples of such species or selectors suitable for use in the context of the embodiments described herein.

In some cases, fabrication methods described herein may advantageously allow for rapid screening of a wide range of materials or combination of materials for use in a particular application and/or device. For example, rapid prototyping of a large number of chemiresistive gas and vapor sensors can be achieved. As shown in FIGS. 1A-D, physical or mechanical abrasion of an article containing a material on the surface of a substrate may be rapidly performed to produce a prototype device. The prototype devices may each contain a different conductive material, a different selector or species, different mass ratios of conductive material to selector/species, and/or may differ in other device characteristics, such as film thickness, electrode materials, device configuration, and the like. Evaluation of the performance of each prototype device may be performed to identify the device appropriate for use in a particular application. Subsequent fabrication of larger devices, or larger numbers of devices, may optionally be performed using a similar fabrication method as described herein, and/or other methods, including chemical vapor depositions, drop-casting, spin-coating, spray-coating, inkjet printing, transfer printing, and the like.

In some cases, fabrication methods described herein may also allow for screening of a wide range of conditions (e.g., reaction time, temperature, analyte concentration, etc.) that may be suitable for a particular application. For example, in the case of sensors, a plurality of identical prototype devices may be fabricated using methods described herein, and each prototype device may be placed under a different set of conditions in order to optimize device performance. In some cases, the prototype devices may be placed under conditions which vary in temperature, pH, type of atmosphere (e.g., nitrogen, oxygen, etc.), potential, current, analyte, exposure time to analyte, concentration of analyte, and the like.

Devices for forming a circuit and/or determining analytes are also provided. In certain embodiments, the device comprises a substrate comprising a first portion and a second portion adjacent the first portion, a material deposited on the first portion, wherein the first portion has a different average affinity for the first material than the second portion. In some embodiments, the device further comprises a first electrode, a second electrode, and a material arranged in electrochemical communication with the first and the second electrodes. The material may include a conductive material (e.g., a carbon-based nanostructure), such that resistance to current flow between the first and second electrode is affected by the material. Upon exposure to an analyte, the analyte may interact with the material to affect resistance to current flow between the first and second electrodes, thereby generating a signal in the device by which the analyte is determined. In some embodiments, the material is in substantially solid form.

An analyte, or a change in the environment surrounding the device, may be determined by monitoring, for example, a change in a signal of a species or material present within the device. The change in signal may be associated with an interaction (e.g., covalent bonding, non-covalent bonding) between the device (e.g., species) and the analyte. The signal may comprise an electrical, optical, or other property of the device. For example, the device may have a resistance that is affected by the presence of an analyte. As used herein, the term "determining" generally refers to the analysis of a species or signal, for example, quantitatively or qualitatively (whether the analyte is present and/or in what amount or concentration), and/or the detection of the presence or absence of the species or signals. "Determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte. In some cases, devices described herein may be useful as sensors for analytes such as explosives, chemical warfare agents, and/or toxins.

In some cases, the analyte may be present in a part-per-million concentration. In some cases, the analyte may be present in a part-per-billion concentration.

In some embodiments, interaction between the device and an analyte produces a change in an electrical or electrochemical property of the device. For example, the material (e.g., a conductive material (e.g., carbon nanotubes)) may be arranged in electrical communication with two electrodes and may have a particular current, voltage, conductivity, and/or resistance (e.g., signal). Upon interaction with an analyte, the current, voltage, conductivity, and/or resistance of the device may be affected (e.g., may increase or decrease) such that a change in signal is produced. In some cases, the change in signal may be associated with a charge transfer reaction and/or binding interaction between the material and the analyte. In some cases, the change in the signal may be associated with a change in the orientation and/or arrangement of the material. In some cases, the change in signal may, be attributed to a physical or chemical disruption in the conductive pathways between conductive species (e.g., carbon nanotubes) of the device.

In some cases, the device may comprise additional components or species that may facilitate interaction between the device and analyte, or otherwise enhance performance of the device. In some cases, the additional component may improve the ability of the device to produce a signal or to respond to an analyte. The additional component may associate with the device such that it enhances an electrical, optical, or other property of the device. In some cases, the additional component may act as a dopant for a conductive species (e.g., carbon nanotube) present within the device. For example, the device may comprise a species capable of associating with carbon nanotubes present within the device. In some embodiments, the device includes a species that may interact with the carbon nanotubes via pi-stacking interactions.

The device may comprise additional components, such as a detector component positioned to detect the signal. In one set of embodiments, the device may be a chemiresistor device, wherein the device exhibits changes in electrical resistance upon exposure to an analyte. Chemiresistors may be advantageous in that the resistance changes can be read-out by a simple, low power and low current circuit. In other embodiments, a device of the present invention may exhibit signals, or changes in signals, that may be determined using Raman spectroscopy, adsorption and/or emission photophysics, ellipsometry, atomic force microscopy, scanning electron microscopy, electrode passivation, and the like.

In some embodiments, simple screening tests may be conducted to select appropriate materials (e.g., carbon nanotubes), species, device configuration, set of conditions, etc., to suit a particular application. In some cases, a material or device may be screened to determine the sensitivity and/or stability of the material or device. In some cases, a material (and/or device) may be selected based on an ability to detect one or more analytes. For example, the ability of a device to detect an analyte may be determined by comparing the signal (e.g., conductance) of the device prior to and following exposure to an analyte. In another example, a device may be exposed to varying concentrations of an analyte to determine the sensitivity of the device.

In some cases, the device may determine changes in a condition, or set of conditions, of a surrounding medium. As used herein, a change in a "condition" or "set of conditions" may comprise, for example, change to a particular temperature, pH, solvent, chemical reagent, type of atmosphere (e.g., nitrogen, argon, oxygen, etc.), electromagnetic radiation, or the like. In some cases, the set of conditions may include a change in the temperature of the environment in which the device is placed. For example, the device may include a component (e.g., species) that undergoes a chemical or physical change upon a change in temperature, producing a determinable signal from the device.

Articles suitable for use in methods described herein may be fabricated using various methods. Typically, the article comprising the material is in solid form (e.g., a pellet, pencil, etc.), and may, in some cases, exhibit improved stability relative to solutions, suspensions, dispersions, slurries, etc., containing such materials. The article may be referred to herein as a "Process Enhanced NanoCarbon for Integrated Logic" or "PENCIL." In some embodiments, the article is prepared by compression of a powder that includes the material. In some embodiments, the article is prepared by mechanical mixing (e.g., ball milling) a powder that includes the material, followed by compression of the powder to form the article. In some embodiments, the article is prepared from a solution including the material. Such articles or "PENCILs" can be used repeatedly for the fabrication of multiple sensors, using methods described herein. In some cases, a functional device (e.g., sensor) may be fabricated using a relatively small amount of material, e.g., <5 µg.

In some cases, the article contains both the material (e.g., a carbon-based nanostructure or nanostructured carbon) and the species responsive to an analyte or to a change in a surrounding medium or environment. For example, the article may be a solid composite of the material and the species. In one set of embodiments, the material may be mechanically mixed (e.g., ball milled) with a species or selector, forming a blended powder. In some cases, the mechanical mixing may involve ball milling, including liquid- or solvent-assisted ball milling as well as ball milling at different temperatures. In some embodiments, the method may involve ball milling a material and species, if present, that have been cooled cryogenically prior to mixing, for example, to enhance inelastic collision efficiency. In some embodiments, the method may involve ball milling a material and species, if present, that have been heated, for example, to add energy to the system and facilitate annealing.

The blended powder may then been compressed into an article (e.g., pellet, rod, or other shape) with a hydraulic press, and subsequently deposited onto a substrate by mechanical abrasion to produce a conductive layer of material selective for specific analytes or specific changes in a set of conditions. For example, carbon nanotubes may be ball-milled with various molecules designed for selective capture of vapors, and the resulting blended powder may be compressed into a pellet. Mechanical abrasion between the pellet and a substrate may be performed to form a material responsive to an analyte or changes in a set of conditions.

In some embodiments, the material, and optionally additional components, may be combined with a fluid carrier (e.g., solvent) and stirred, vortexed, sonicated, or the like. The resulting mixture may be subsequently dried into a solid form by evaporation, spray drying, heating, freeze-drying, compression, or other methods, to produce the article.

Devices as described herein may have various device configurations, and may be selected to suit a particular application. For example, the material may be fabricated such that a first and the second electrode are in electrochemical communication with the material. The device may be used as a sensor, circuit, a capacitor, a tag for remotely-monitored sensors, a label or tracker for a subject or object, a photovoltaic device, a resistor, a fuse, a transistor, an antenna, or in other applications. Those of ordinary skill in the art would be able to select suitable materials (e.g., conductive materials, species, substrates, electrode materials, etc.) for a particular application.

In some embodiments, a plurality of devices may be arranged to form an array of devices capable distinguishing, identifying, and quantifying a variety of different analytes simultaneously. For example, in an array of devices, each individual device can include a species responsive to an analyte. In some cases, a first device of the array may include a species responsive to a first analyte and a second device of the array may include a species responsive to a second analyte, wherein the first and second analytes are different.

As described herein, in some cases, a single device may be fabricated within about 60 minutes or less (e.g., within about 60 minutes, within about 45 minutes, within about 30 minutes, within about 15 minutes, within about 10 minutes, within about 5 minutes). In such cases, the act of fabricating the single device consists essentially of the acts of (1) forming the article comprising the material and, optionally, the species responsive to an analyte and/or to a change in a set of conditions; (2) forming the material and species, if present, on the surface of the substrate with the article (e.g., via physical abrasion); and (3) arranging an electrode material in electrochemical communication with the material and species, if present. In one embodiment, the first step may be performed in about 5 minutes, while the second and third steps may be performed in about 5 minutes; that is, the fabrication of a single device may be performed in about 10 minutes.

In some cases, the method may involve fabricating a plurality of devices. For example, multiple devices can be fabricated, each device including a different sensor material, and the performance of each device may be evaluated in order to screen for which sensor material is suitable for a particular application. In some cases, multiple chemiresistor devices may be fabricated, each device including a different sensor material, and the change in resistance of each device upon exposure to an analyte, or to a change in environment, may be evaluated in order to screen for which sensor material is suitable for a particular application.

As used herein, the term "nanostructure" refers to any chemical structure having at least one dimension on the order of nanometers. In some cases, the nano structure has an elongated chemical structure having a diameter on the order of nanometers and a length on the order of microns to millimeters, resulting in an aspect ratio greater than 10, 100, 1000, 10,000, or greater. In some cases, the nanostructure may have a diameter less than 1 µm, less than 100 nm, 50 nm, less than 25 nm, less than 10 nm, or, in some cases, less than 1 nm. The nanostructure may have a cylindrical or pseudo-cylindrical shape. In some cases, the nanostructure may be a nanotube, such as a carbon nanotube. In some cases, the nanostructure is a nanorod, nanowire, or nanoribbon. In some cases, the nanostructure is a nanoparticle.

As used herein, the term "carbon nanotube" is given its ordinary meaning in the art and refers to a substantially cylindrical molecule, in some cases, comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than about 100, greater than about 1000, greater than about 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The carbon nanotubes may be functionalized or substituted with a wide range of functional groups. Examples of functional groups that carbon nanotubes may be substituted with include peptides, proteins, DNA, RNA, peptide nucleic acids (PNA), metal complexes, ligands for metals, ligands for proteins, antibodies, polarizable aromatics, crown ethers, hydroxyl amines, polymers, initiators for polymerizations, liquid crystals, fluorocarbons, synthetic receptors, and the like. The properties of the nanotubes may also be tailored based on the substitution of the fused, aromatic network. Those skilled in the art would recognize what types of functional groups would afford a particular, desired property, such as increased solubility, or the ability to determine an analyte.

Substituted carbon nanotubes may be synthesized using various methods, including those described in Zhang et al., J. Am. Chem. Soc. 2007, 129(25), 7714; International Publication No. WO2008/133779, which are incorporated herein by reference in their entirety for all purposes.

In some cases, the material may comprise nanoparticles. As used herein, the term "nanoparticle" generally refers to a particle having a maximum cross-sectional dimension of no more than 1 µm. Nanoparticles may comprise inorganic or organic, polymeric, ceramic, semiconductor, metallic, non-metallic, magnetic, crystalline (e.g., "nanocrystals"), or amorphous material, or a combination of two or more of these. The nanoparticles may be also selected to be positively or negatively charged. Typically, nanoparticles may have a particle size less than 250 nm in any dimension, less than 100 nm in any dimension, or less than 50 nm in any dimension. In some embodiments, the nanoparticles may have a diameter of about 2 to about 50 nm. In some embodiments, the nanoparticles may have a diameter of about 2 to about 20 nm. The particle size may be measured by methods known in the art, such as electron microscopy.

Polymers or polymer materials, as used herein, refer to extended molecular structures comprising a backbone (e.g., non-conjugated backbone, conjugated backbone) which optionally contain pendant side groups, where "backbone" refers to the longest continuous bond pathway of the polymer. In some embodiments, the polymer is substantially non-conjugated or has a non-conjugated backbone. In some embodiments, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. It should be understood that other types of conjugated polymers may be used, such as sigma-conjugated polymers.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. The band gap and/or selectivity for particular analytes can be achieved by modification or incorporation of different polymer types, as would be understood by those of ordinary skill in the art. The polymer compositions can vary continuously to give a tapered block structure and the polymers can be synthesized by either step growth or chain growth methods.

The number average molecular weight of the polymer may be selected to suit a particular application. As used herein, the term "number average molecular weight (Mn)" is given its ordinary meaning in the art and refers to the total weight of the polymer molecules in a sample, divided by the total number of polymer molecules in a sample. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

The device may also comprise an insulating material. The insulating material may be arranged between the material and one or more electrodes and/or the substrate. Examples of suitable insulating materials include, but are not limited to, polysilicate glass, silicon dioxide, silicon nitride, and the like.

As used herein, the term "electrode" or "electrode material" refers to a composition, which, when connected to an electronic device, is able to sense a current or charge and convert it to a signal. An electrode may be comprised of a material or combination of materials such as, for example, metals. Non-limiting examples of suitable metals include gold, copper, silver, platinum, nickel, cadmium, tin, and the like. The electrodes may also be any other metals and/or non-metals known to those of ordinary skill in the art as conductive (e.g. ceramics). The electrodes may be deposited on a surface via vacuum deposition processes (e.g., sputtering and evaporation), solution deposition (e.g., electroplating or electroless processes), or screen printing. In a specific example, gold electrodes are deposited by thermal evaporation.

In some embodiments, the material may comprise a conductive, semiconductive, semimetallic species, or other species capable of transporting charge to create a conductive pathway. The conductive, semiconductive, or semimetallic species may include inorganic materials (e.g., metals, alloys, semiconductors), organic materials (e.g., polymer materials), organometallic materials, and/or combinations thereof. In some cases, the material may include a plurality of nanostructures (e.g., nanotubes, nanowires, nanoribbons, nanoparticles, etc.). The nanostructures may be selected to exhibit, for example, high charge mobilities and/or resistance to damage from ionizing radiation. In some cases, mixtures or assemblies of nanostructures may be utilized. Some embodiments may involve the use of carbon nanotubes, such as single-walled carbon nanotubes (SWCNTs) and/or multi-walled carbon nanotubes (MWCNTs), which can display relatively high charge mobilities (e.g., 100,000 $cm^2/Vs$ for SWCNTs). In some cases, nanowires, such as gold, silver, copper, bismuth, gadolinium nanowires, silicon, may be used as the conductive species. In some cases, the conductive, semiconductive, or semimetallic species may comprise nanoparticles (e.g., gold nanoparticles).

As used herein, an "analyte" can be any chemical, biochemical, or biological entity (e.g. a molecule) to be analyzed. The analyte may be in vapor phase, liquid phase, or solid phase. In some embodiments, the analyte is a vapor phase analyte. In some cases, the analyte may be a form of electromagnetic radiation. In some cases, the device may be selected to have high specificity for the analyte, and may be a chemical, biological, or explosives sensor, for example. In some embodiments, the analyte comprises a functional group that is capable of interacting with at least a portion of the device (e.g., a species). In some cases, the device may determine changes in pH, moisture, temperature, and the like, of a surrounding medium. The analyte may be a chemical species, such as an explosive (e.g., TNT), toxin, or chemical warfare agent. In a specific example, the analytes are chemical warfare agents (e.g., sarin gas) or analogs of chemical warfare agents (e.g., dimethyl methylphosphonate, DMMP). In some embodiments, the analyte comprises ethylene (e.g., to monitor the ripeness of produce).

In some embodiments, the analyte may be an aromatic species, including optionally substituted aryl species and/or optionally substituted heteroaryl species, such as benzene or toluene. In some embodiments, the analyte may be an amine-containing species such as ammonia. In some embodiments, the analyte may be a nitrile-containing species such as acetonitrile. In some embodiments, the analyte may be an oxygen-containing species, such as a species comprising an alcohol, a ketone, an ester, a carboxylate, an aldehyde, other carbonyl groups, an ether, or the like. In some embodiments, the analyte may be a species comprising a ketone, an ester, an ether, or an aldehyde, such as cyclohexanone, ethyl acetate, THF, or hexanal. In some embodiments, the analyte is a phosphorus-containing analyte such as DMMP. In some embodiments, the analyte may be a nitro-containing species such as nitromethane or TNT. Other examples of analytes include alcohols, olefins, nitric oxide, thiols, thioesters, and the like.

Specific examples of analytes include nitromethane, benzene, toluene, o-xylene, m-xylene, p-xylene, mesitylene, nitrobenzene, cyano-benzene, hexane, hexene, hexenal, ethylene, 1-methylcyclopropene, propene, butenes, isoprene, cyclohexanone, acetone, tetrahydrofuran (THF), methanol, ethanol, isopropanol, hexanal, DMMP, acetonitrile, nitromethane, ethyl acetate, methyl acetate, water, dimethyformamide (DMF), formaldehyde, dimethylsulfide, ethylene, or ammonia.

As used herein, an "aromatic species" includes unsubstituted or substituted, monocyclic or polycyclic aromatic ring or ring radical, including unsubstituted or substituted monocyclic or polycyclic heteroaromatic rings or ring radicals (e.g., aromatic species including one or more heteroatom ring atoms). Examples of aromatic species include phenyl, naphthyl, anthracenyl, chrysenyl, fluoranthenyl, fluorenyl, phenanthrenyl, pyrenyl, perylenyl, and the like.

As used herein, "aryl" means a monocyclic or polycyclicaromatic ring or ring radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro.

As used herein, "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like. Other embodiments suitable for use in the context of the embodiments described herein are described in International Pat. Apl. Serial No.: PCT/US2009/001396, filed Mar. 4, 2009, entitled, "Devices and Methods for Determination of Species Including Chemical Warfare Agents"; International Pat. Apl. Serial No.: PCT/US2009/006512, filed Dec. 11, 2009, entitled, "High Charge Density Structures, Including Carbon-Based Nanostructures and Applications Thereof"; U.S. patent application Ser. No. 12/474,415, filed May 29, 2009, entitled, "Field Emission Devices Including Nanotubes or Other Nanoscale Articles"; International Pat. Apl. Serial No.: PCT/US2011/051610, filed Oct. 6, 2010, entitled, "Method and Apparatus for Determining Radiation"; International Pat. Apl. Serial No.: PCT/US2010/055395, filed Nov. 4, 2010, entitled, "Nanostructured Devices including Analyte Detectors, and Related Methods"; International Pat. Apl. Serial No.: PCT/US2011/053899, filed Sep. 29, 2011, entitled, "COMPOSITIONS, METHODS, AND SYSTEMS COMPRISING POLY(THIOPHENES); and International Pat. Apl. Serial No.: PCT/US2011/025863, filed Feb. 23, 2011, entitled, "Charged Polymers and Their Uses in Electronic Devices", which applications are incorporated herein in their entireties for all purposes.

EXAMPLES AND EMBODIMENTS

Example 1

Figure 1B:
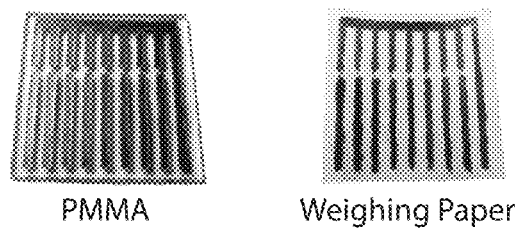
Figure 1C:
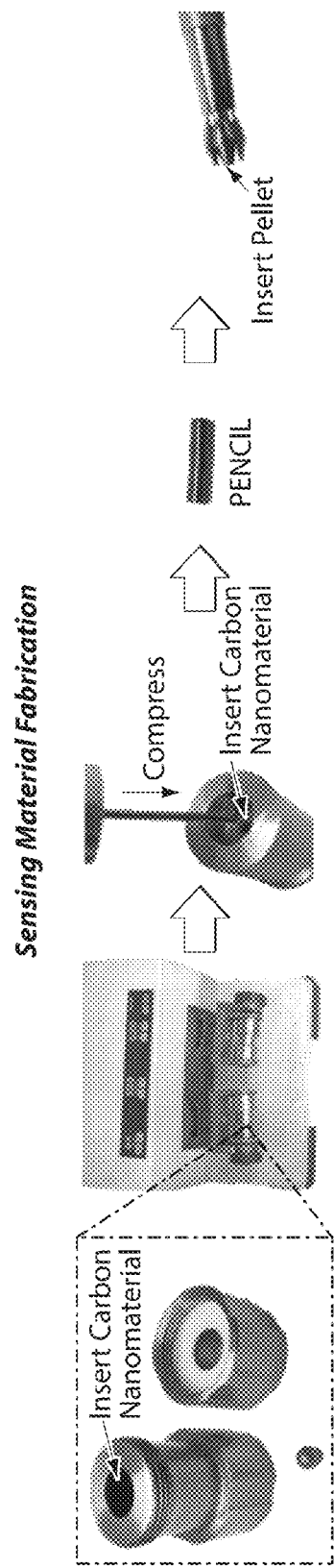
Figure 1D:
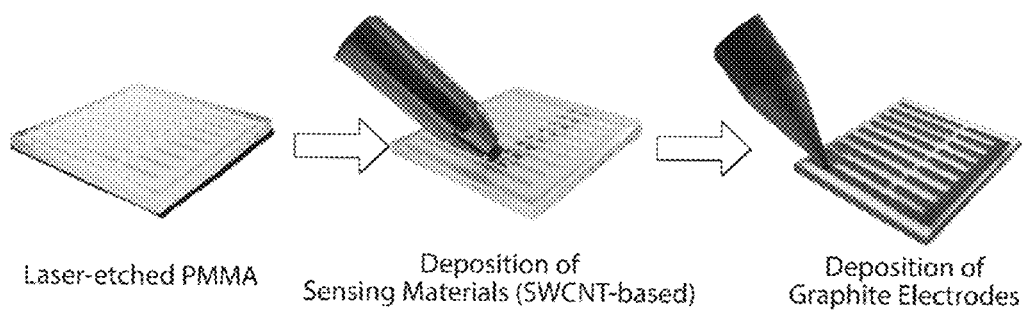

Various devices, including chemiresistive chemical sensors, were fabricated using the methods described herein. Sensing materials (e.g., SWCNT-based) and graphite as electrodes were both deposited by mechanical abrasion to yield partially-drawn and fully-drawn, chemiresistive gas-sensors on various unmodified substrates such as adhesive tape and unpolished silicon wafers (FIG. 1A), and laser-etched substrates such as PMMA and weighing paper (FIG. 1B). FIG. 1C illustrates fabrication of a sensing material comprising mechanically mixing and compressing SWCNT composites into a pellet. FIG. 1D is an exemplary illustration of stepwise fabrication of fully drawn chemiresistive sensors on PMMA.

Example 2

The following example describes the fabrication of PENCILs.

Triethyl citrate, 1-ethyl-3-methylimidazolium tetrafluoroborate, 2-(4-Aminophenyl)-1,1,1,3,3,3-hexafluoro-2-propanol, and 1-n-Butyl-3-methylimidazolium hexafluorophosphate were used as selectors to mixed with SWCNTs. Purified SWCNTs (>95% SWCNTs) were obtained from commercial sources. All chemicals and reagents were used without further purification, unless noted otherwise. SWCNTs, selector, and 7 mm diameter stainless steel grinding balls were added into a 5 ml stainless steel ball milling vial. The vial was placed into a mixing mill where the carbon material was mechanically mixed at 30 Hz for 5 min under ambient conditions. The SWCNTs:selector mixture was then placed into a custom-made stainless steel pellet mold with 2 mm internal diameter where the SWCNT composites were compressed for 1 min to make PENCILs.

Example 3

The following example describes etching procedures for use in the methods described herein.

For laser-etching, a 60 Watt laser was used. The power, speed, and pulses-per-inch settings were adjusted to provide suitable etching on each substrate type. A listing of such parameters for exemplary substrates are included in Table 1.

TABLE 1

| Material | Power | Speed | Pulses-per-inch (PPI) |
|---|---|---|---|
| Weighing paper | 15 | 100 | 1000 |
| PMMA | 20 | 50 | 500 |
| Glass | 10 | 10 | 1000 |

Table 2 summarizes the average surface roughness of PMMA and glass substrates after laser-etching for different laser power and the average film thickness of SWNTs after an article comprising compressed SWNTs was contacted (i.e. mechanically abraded) with each substrate.

TABLE 2

| Substrate | Average Surface Roughness | Average Film Thickness |
|---|---|---|
| Glass | 4.0 ± 0.3 µm | 1.1 ± 0.3 µm |
| Glass | 3.7 ± 0.3 µm | 1.2 ± 1.1 µm |
| Glass | 2.8 ± 0.3 µm | 0.2 ± 0.6 µm |
| Glass | 0.8 ± 0.2 µm | 0.4 ± 0.4 µm |
| PMMA | 20.4 ± 0.4 µm | 2.5 ± 1.9 µm |
| PMMA | 0.23 ± 0.03 µm | 0.7 ± 0.6 µm |
| PMMA | 3.1 ±0.2 µm | 1.5 ± 1.5 µm |
| PMMA | 8.5 ± 0.2 µm | 4.9 ± 1.4 µm |

For chemical-etching, a thick layer of etching cream was applied to cover the desired surface of glass and allowed to remain for 5 min. All traces of the etching cream were washed with tap water and dried using a stream of nitrogen.

Example 4

Figure 5A:
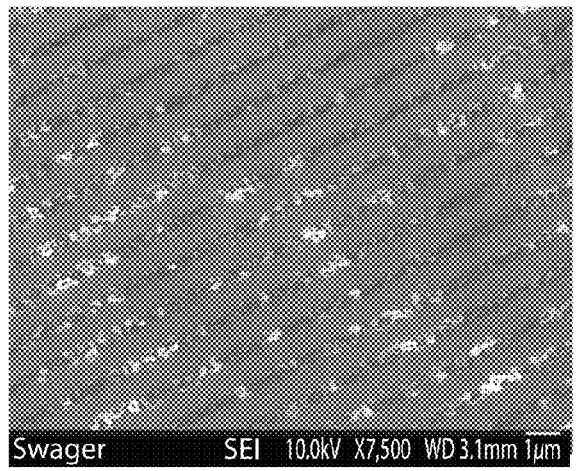
FIGS. 5A-5C show Scanning Electron Microscope (SEM) images of deposition of multiwalled carbon nanotubes deposited on a patterned surface (a diffraction grating film) by mechanical abrasion.
Figure 5B:
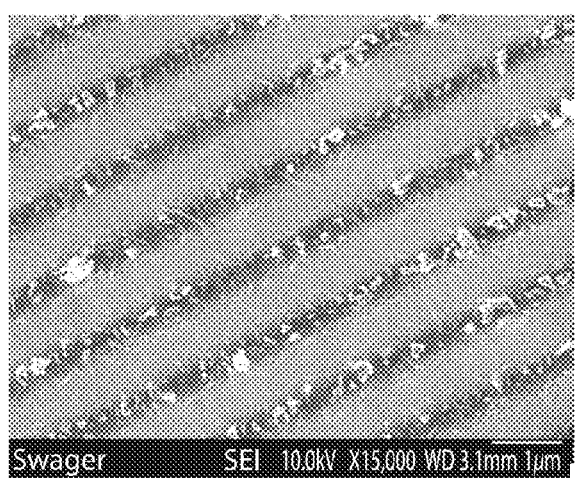
Figure 5C:
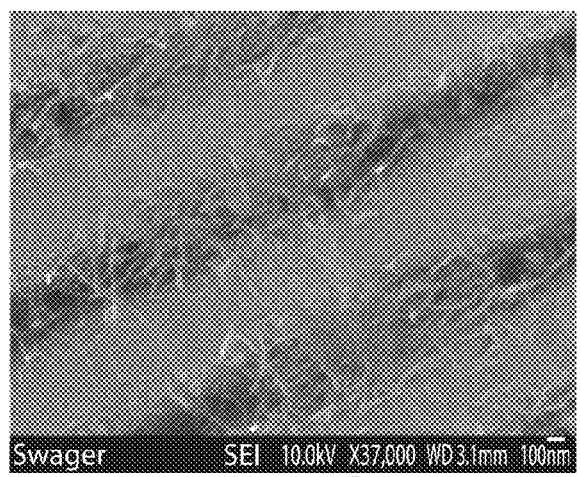
Figure 6:
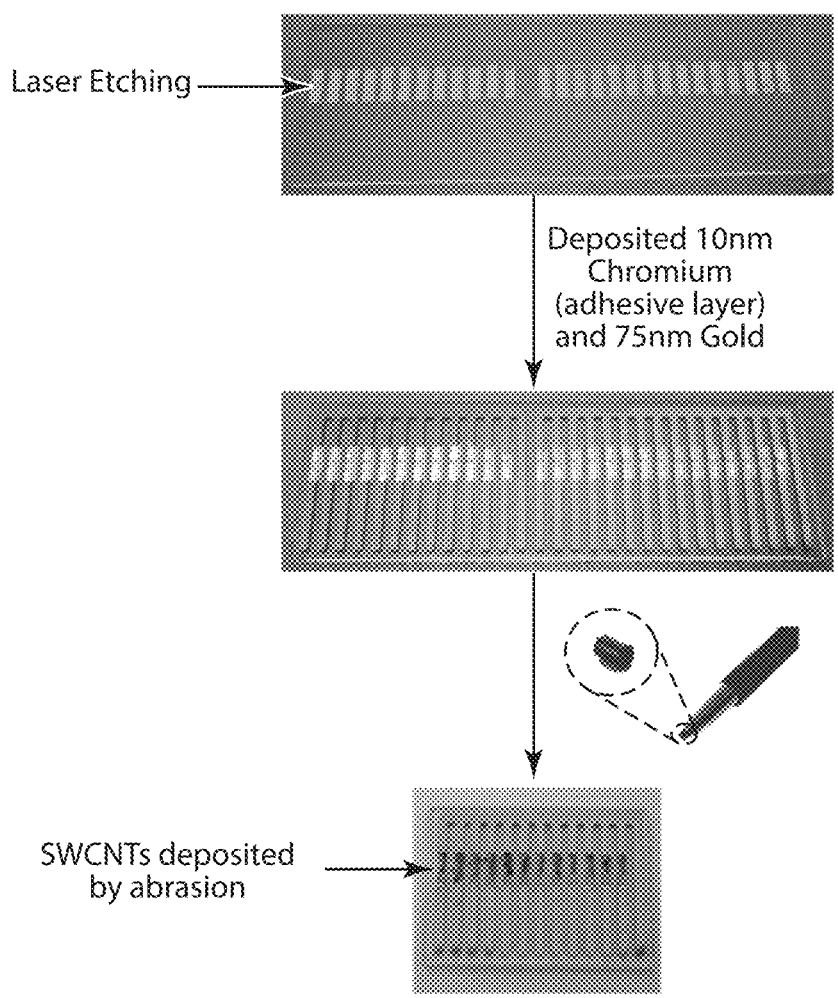
FIG. 6 shows a schematic outline of an exemplary process for fabricating partially-drawn SWCNT-based chemiresistive sensors on laser-etched glass.
Figure 7A:
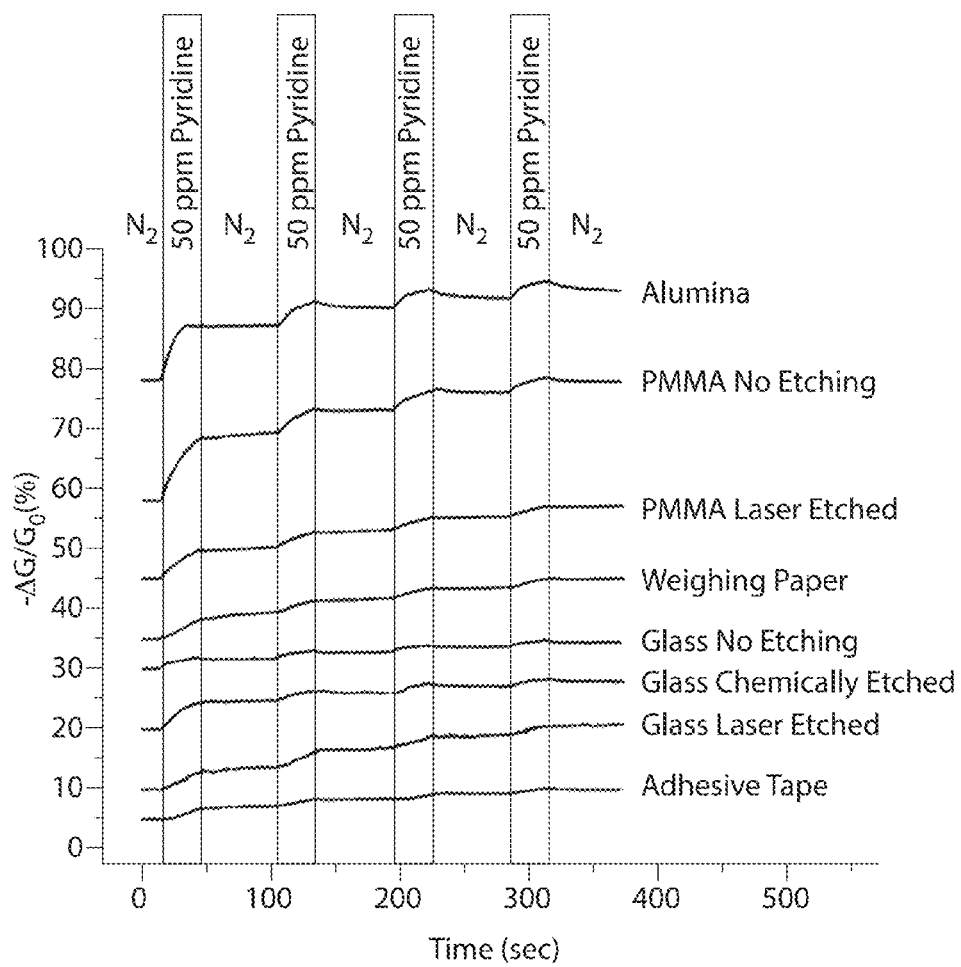
FIGS. 7A-7B shows the sensing response of Pristine SWCNTs devices deposited by abrasion onto various substrates using gold electrodes (0.3 mm gap size), including (FIG. 7A) the normalized change of conductance over time from devices simultaneously exposed four consecutive times to 50 ppm pyridine for 30 s with recovery time of 60 s.
Figure 7B:
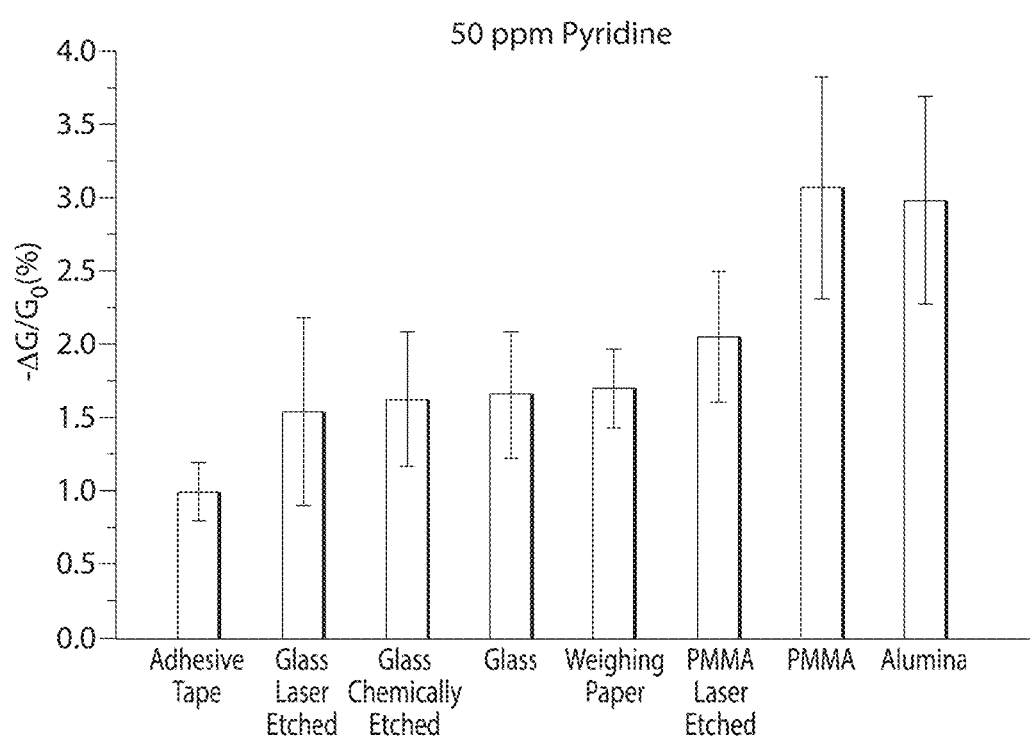
Figure 8A:
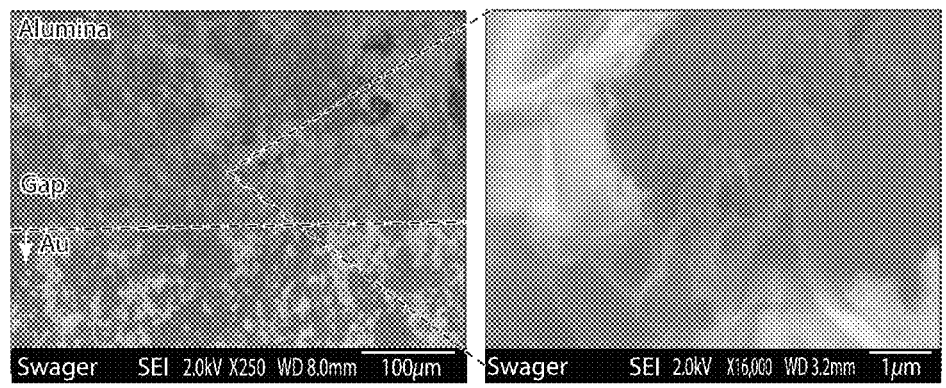
FIGS. 8A-8E shows high resolution Scanning Electron Microscopy (SEM) images of compressed pristine SWCNTs deposited by abrasion between and on top of gold electrodes onto (FIG. 8A) alumina, (FIG. 8B) PMMA, (FIG. 8C) weighing paper, (FIG. 8D) adhesive tape, and (FIG. 8E) glass.
Figure 8B:
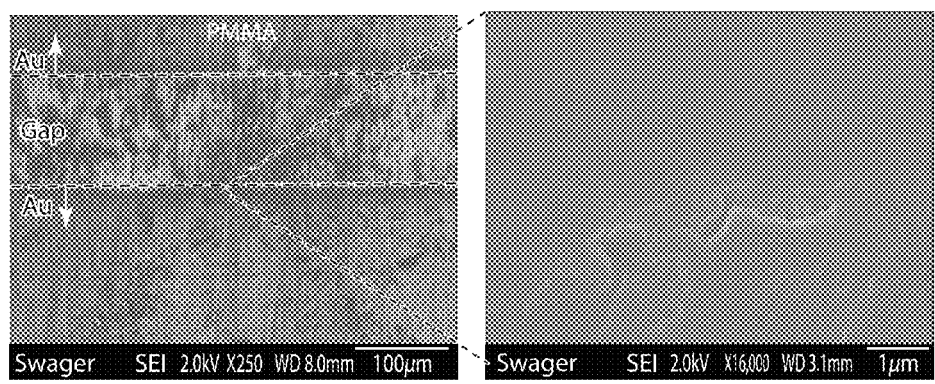
Figure 8C:
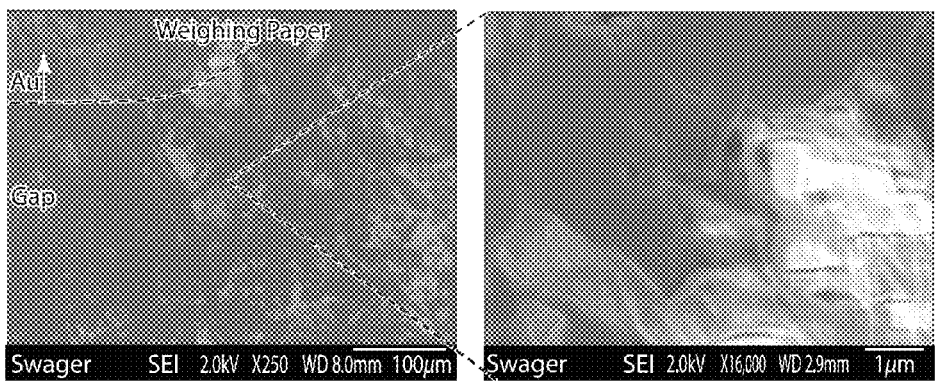
Figure 8D:
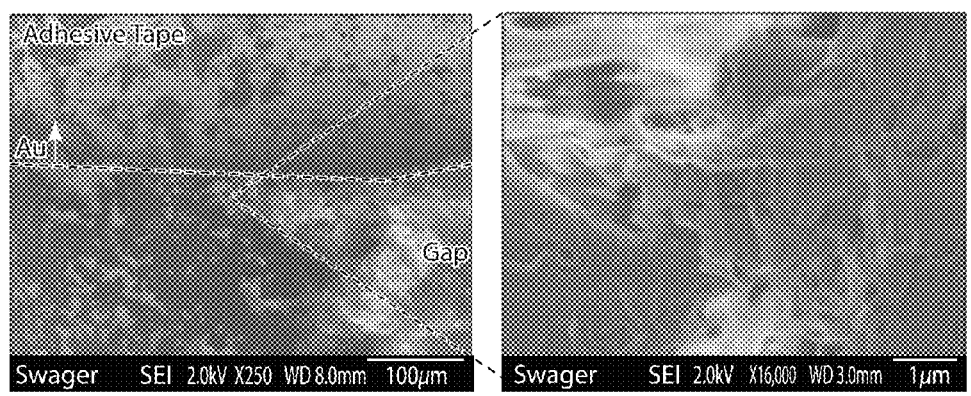
Figure 8E:
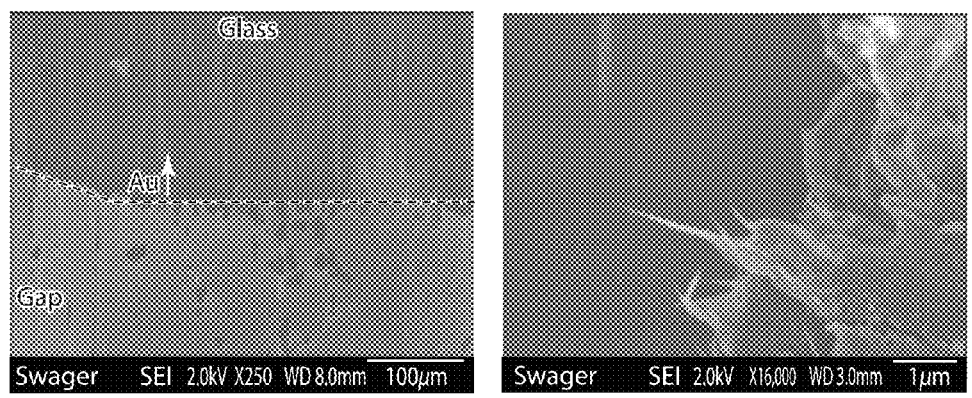

Articles including carbon-based materials on patterns surfaces were fabricated using methods as described herein by mechanical abrasion. FIG. 5A-C shows a Scanning Electron Microscope (SEM) image of multiwalled carbon nanotubes deposited on diffraction grating film with predefined pattern by mechanical abrasion.

Example 2

This example describes the fabrication and characterization of partially-drawn sensors by mechanical abrasion.

The successful stepwise fabrication of fully-drawn chemiresistive sensors consisted of two separate deposition steps: 1) deposition of sensing materials (SWCNTs) and 2) deposition of electrodes (graphite). In order to measure the performance of each deposition step separately, partially-drawn sensors were fabricated and compatibility of various substrates with deposition of resistors with abrasion fabrication techniques (DRAFT) were evaluated. Four substrates to demonstrate the performance and versatility of the fully-drawn sensors were then selected.

Generally, glass slides were cleaned by ultra-sonication in acetone for 30 min and dried using a stream of nitrogen. The glass slides were then cleaned with an UV ozone cleaner for 10 min. PMMA substrates were cleaned by ultra-sonication in soapy water for 15 min followed by sonication in methanol for another 15 min and dried using a stream of nitrogen. Alumina substrates were cleaned by ultra-sonication for 15 min in soapy water and another 15 min in acetone and dried using a stream of nitrogen. Silicon wafer and adhesive tape were used without any further modification.

Using a stainless steel mask, layers of chromium (10 nm) and gold (75 nm) were deposited onto the substrate using thermal evaporation. There was an approximately 1 mm gap between the metal electrodes. The PENCILs were inserted into a holder and deposited using DRAFT (i.e. mechanical abrasion) between and on top of the metal electrodes until about 100 to about 500 kΩ resistance range was achieved on each substrate (as measured across the electrode gap with a multimeter); except for unpolished side of the silicon wafer, where about 6 to about 8 kΩ resistance range was achieved.

Figure 12:
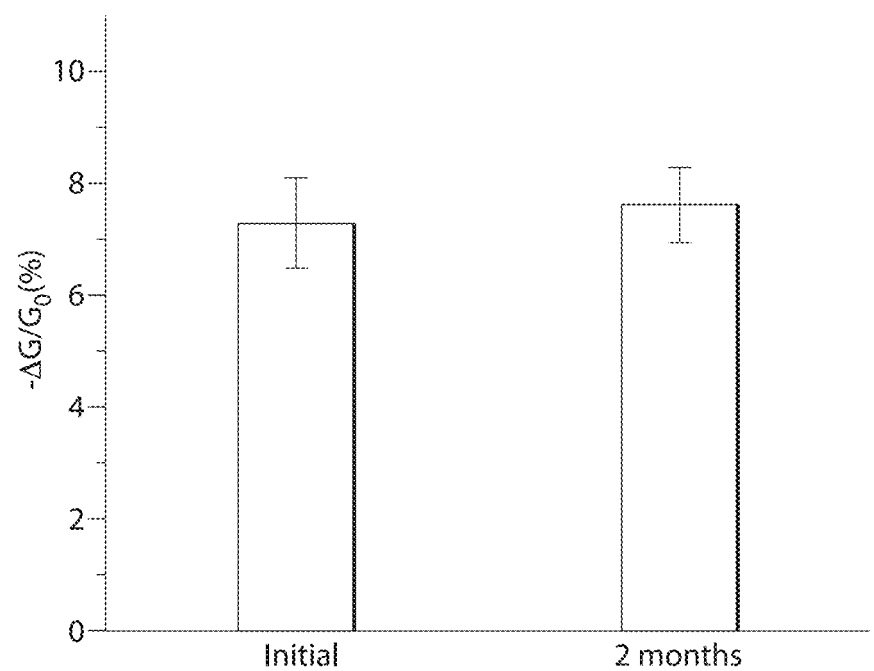
FIG. 12 shows the stability of PENCILs with normalized average conductive responses of at least two sensors simultaneously exposed at least four consecutive times to 50 ppm pyridine (first exposure exempt) for 30 s with a recovery time of 60 s.
Figure 13:
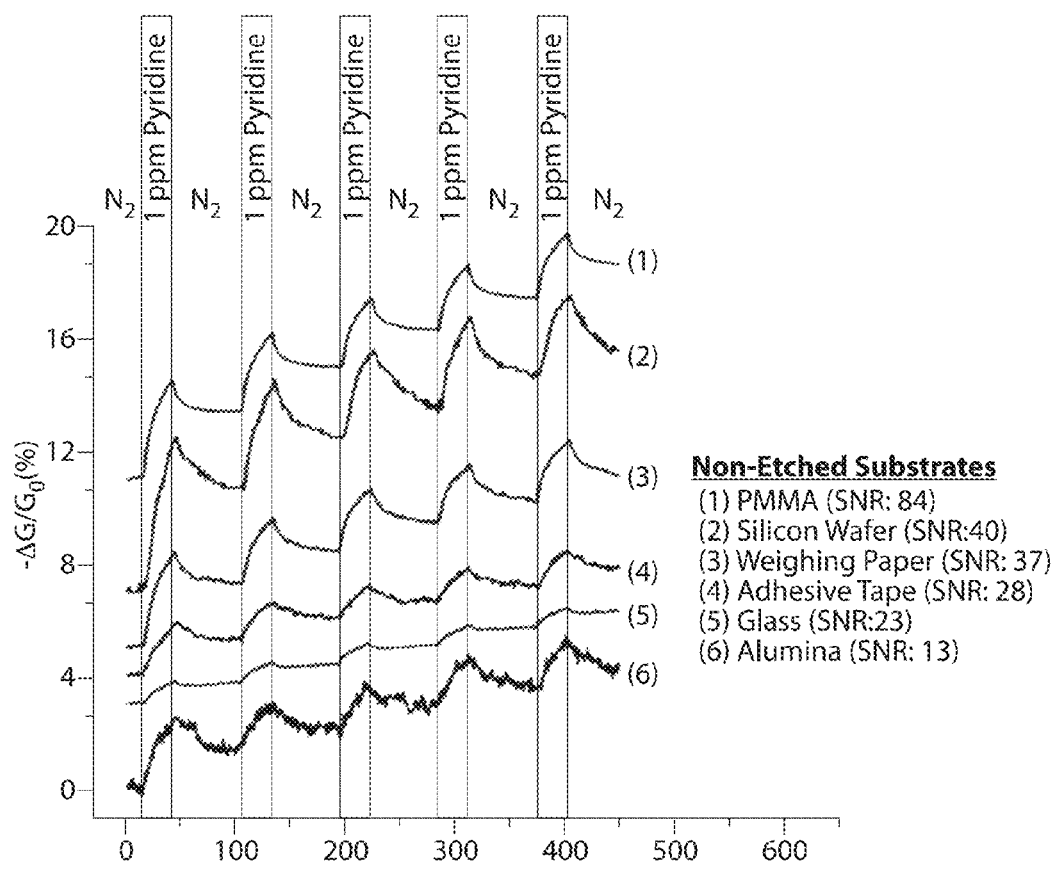
FIG. 13 shows a graph of the sensing responses ($-\Delta G/G_0$, %) with time of a SWCNT-based chemiresistors fabricated on various unmodified substrates after five consecutive exposures to 1 ppm pyridine for 30 s with a recovery time of 60 s.
Figure 14A:
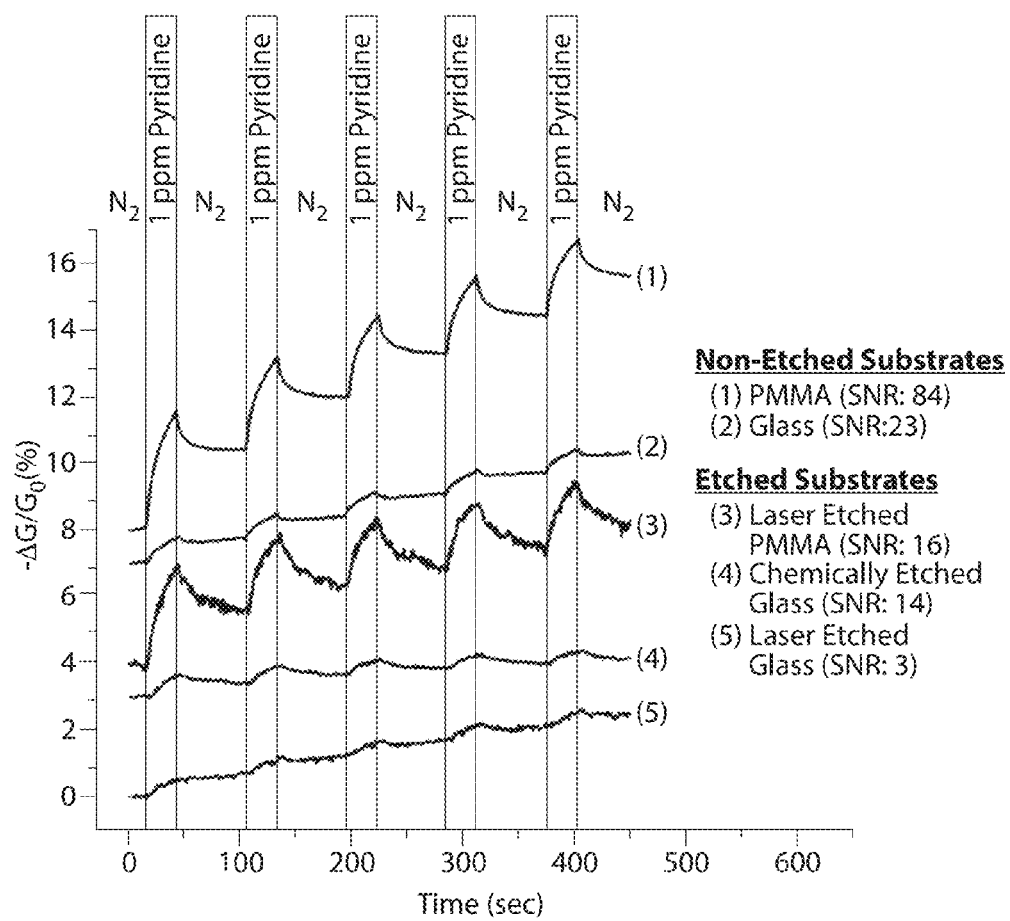
FIGS. 14A-14B shows graphs of the sensing responses ($-\Delta G/G_0$, %) with time of SWCNT-based chemiresistors fabricated on various modified or unmodified substrates after five consecutive exposures to (FIG. 14A) 1 ppm and (FIG. 14B) 50 ppm pyridine for 30 s with recovery time of 60 s.
Figure 14B:
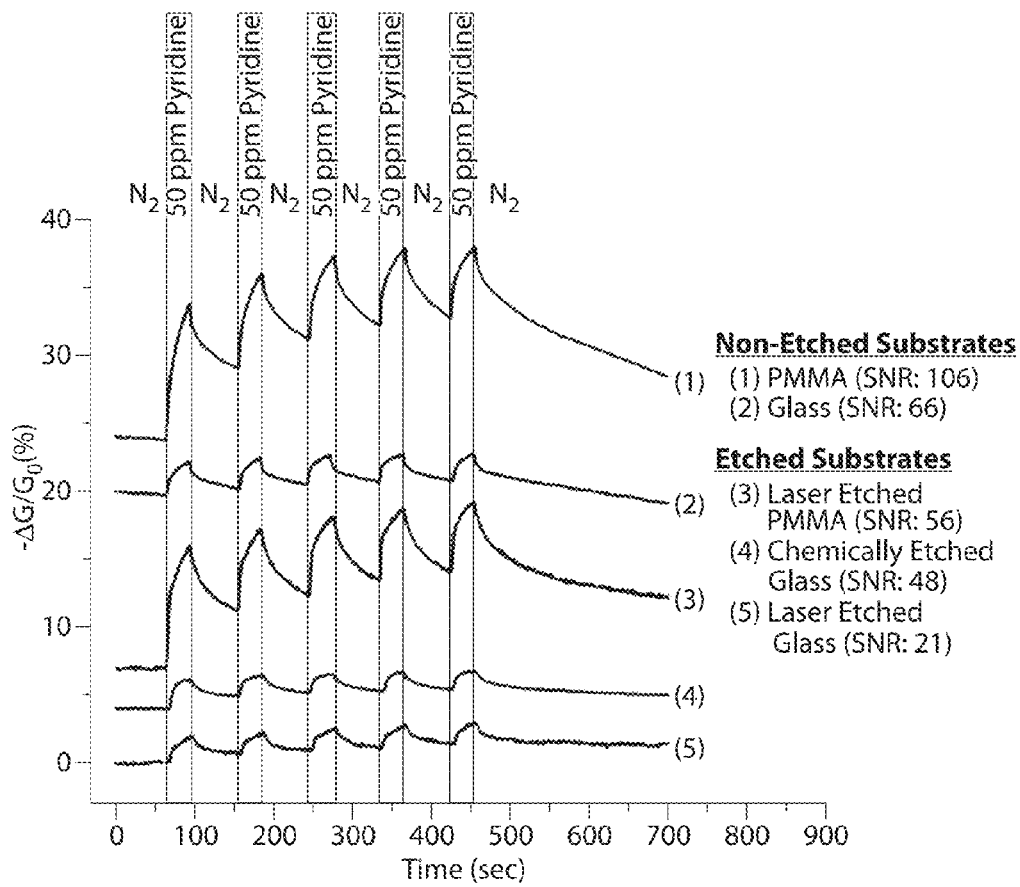
Figure 15A:
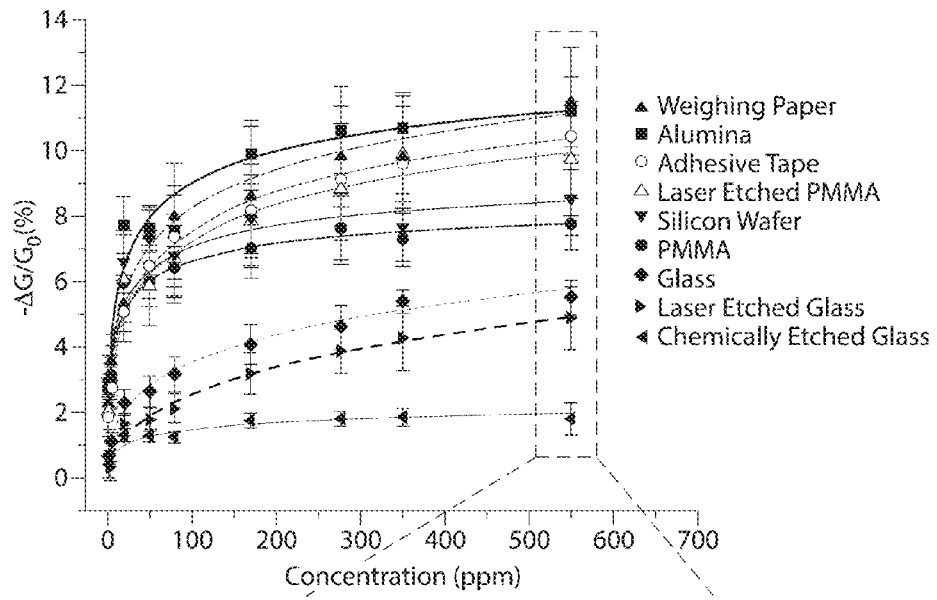
FIGS. 15A-15B shows graphs of the sensing responses ($-\Delta G/G_0$, %) with time of SWCNTs-TEC (2:1 wt. ratio) deposited by abrasion on various substrates between gold electrodes (1 mm gap size), including (FIG. 15A) normalized average conductive responses of various sensors simultaneously exposed five consecutive times to various concentrations of pyridine for 30 s with recovery time of 60 s.
Figure 15B:
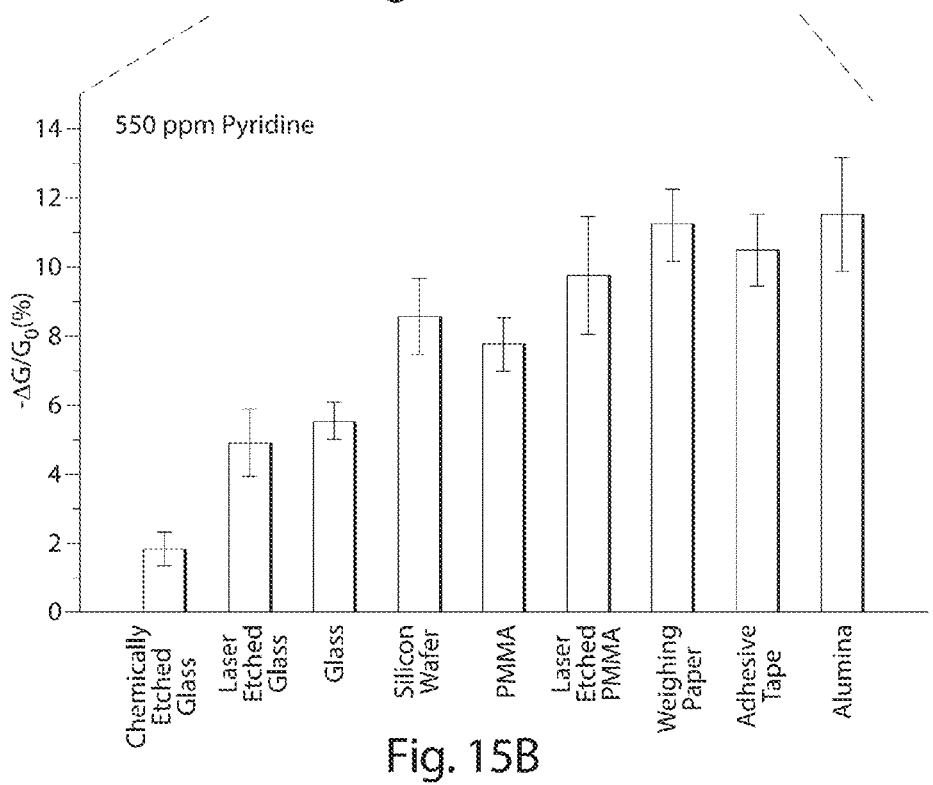

Partially-drawn sensors were made by depositing sensing materials by mechanical abrasion (SWCNT:Selector) between and on top of gold electrodes on six different substrates: weighing paper, glass, silicon, alumina, polymethyl methacrylate (PMMA), and adhesive tape. To evaluate the sensory performance of each device, pyridine was used as a model analyte. To increase the response of the SWCNTs to pyridine vapor, SWCNT composites were made with triethyl citrate (TEC), a commercial, nontoxic, colorless, and odorless liquid used as a food additive and plasticizer. Mechanical mixing and compression of SWCNTs with TEC coated and dispersed SWCNTs within a solid composite of a PENCIL and enabled hydrogen-bonding interactions between the hydroxyl groups of TEC and the lone pair of pyridine, thus enhancing the sensitivity of the SWCNT/TEC composite towards pyridine. PENCILs were stable under ambient conditions and could be used to produce devices over the course of at least two months without any decrease in sensory performance (FIG. 12).

Figure 2A:
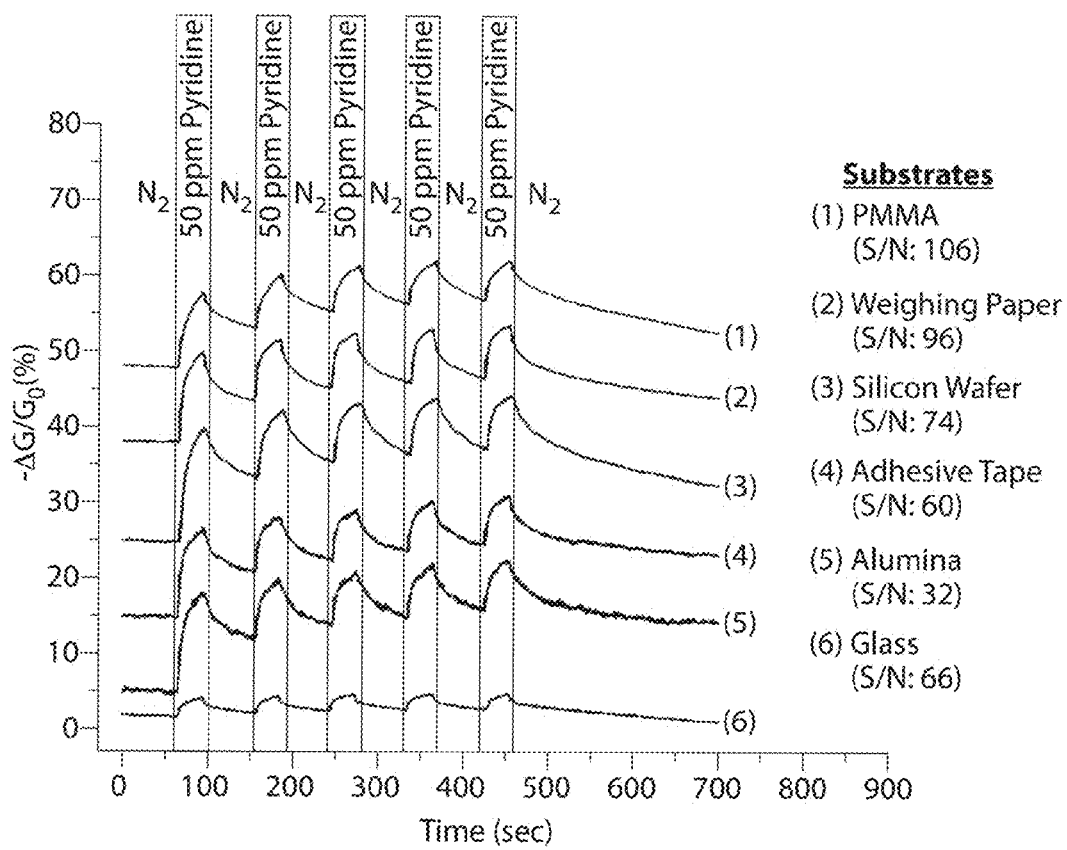
FIGS. 2A-2C shows the response of various devices towards pyridine, including (FIG. 2A) the percent change in normalized conductance with respect to time of devices exposed to 50 ppm pyridine.

To establish compatibility of substrates with DRAFT, devices were fabricated by abrading a composite of SWCNTs and TEC (2:1 wt. ratio) onto six different substrates equipped with gold electrodes (1 mm gap size). The resulting devices generated significant changes in conductance when exposed to 50 ppm pyridine vapour under a constant bias (50 mV). FIG. 2A displays normalized conductance traces of devices exposed five consecutive times to 50 ppm pyridine for 30 s with 60 s recovery time on six different substrates. The functionalized CNT chemiresistors demonstrated a semi-reversible response towards pyridine for all devices. The first exposure provided the largest response consistently.

Figure 2B:
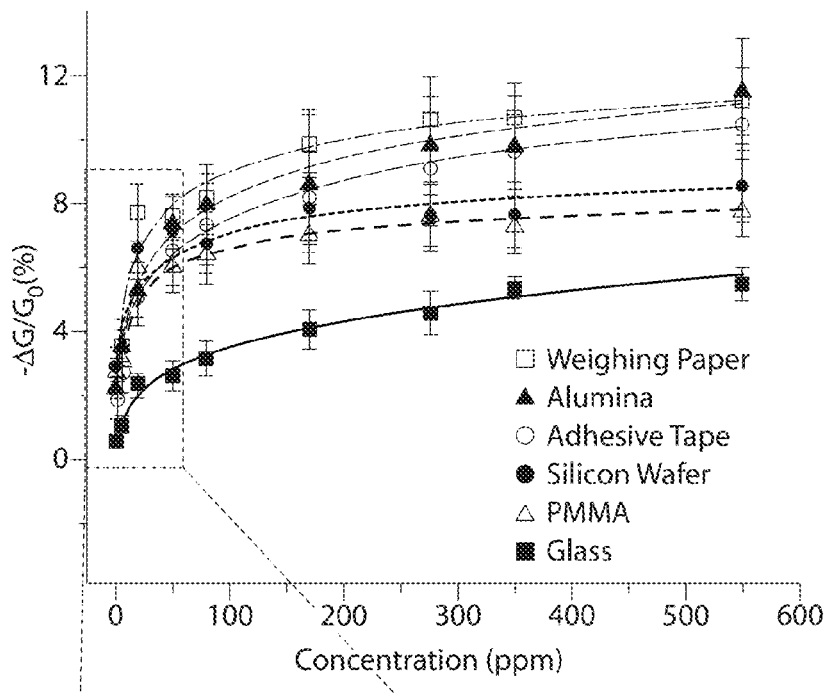
Figure 2C:
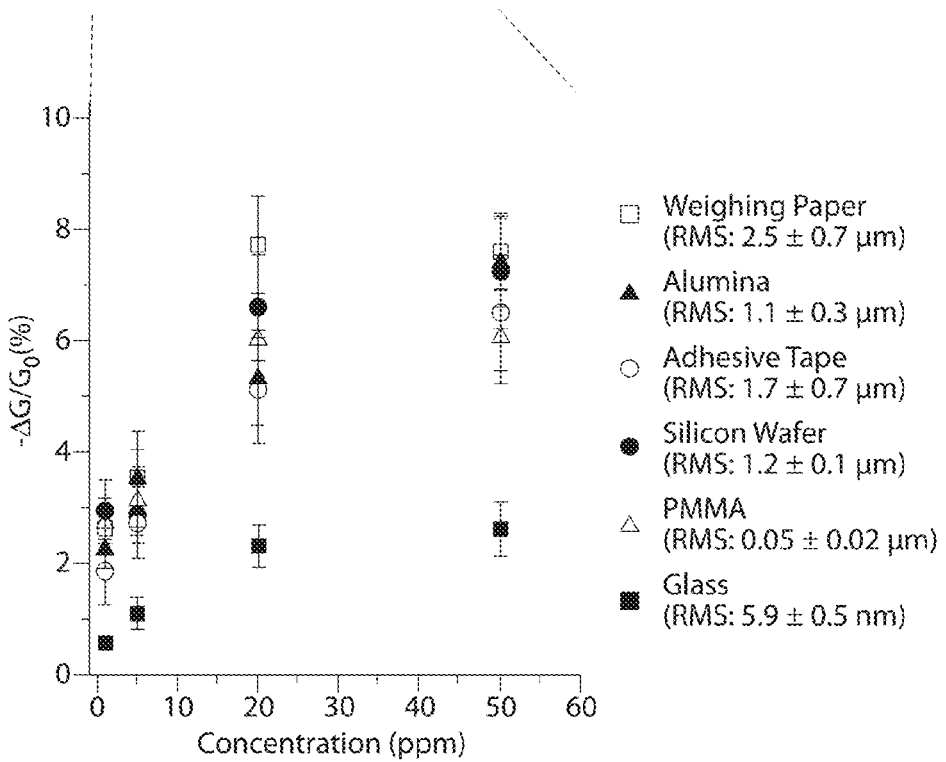
Figure 22:
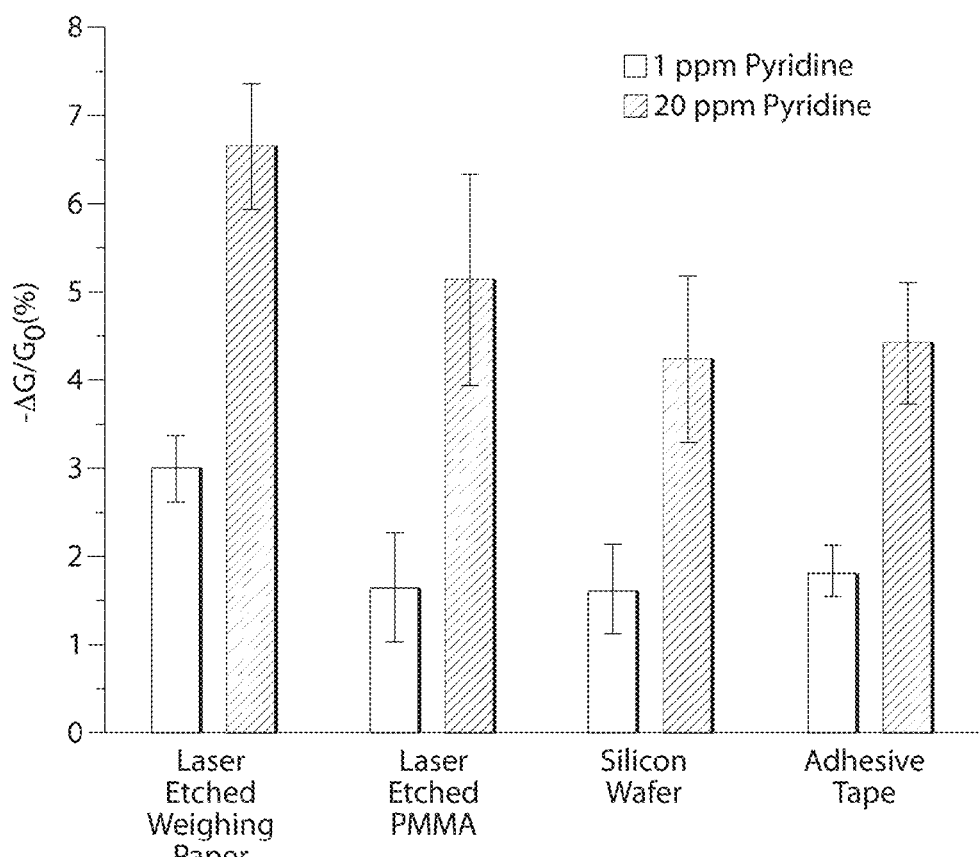
FIG. 22 shows the sensing responses ($-\Delta G/G_0$, %) of at least four fully-drawn sensors simultaneously exposed to 1 ppm and 20 ppm of pyridine for 30 s with 60 s recovery time.
Figure 23:
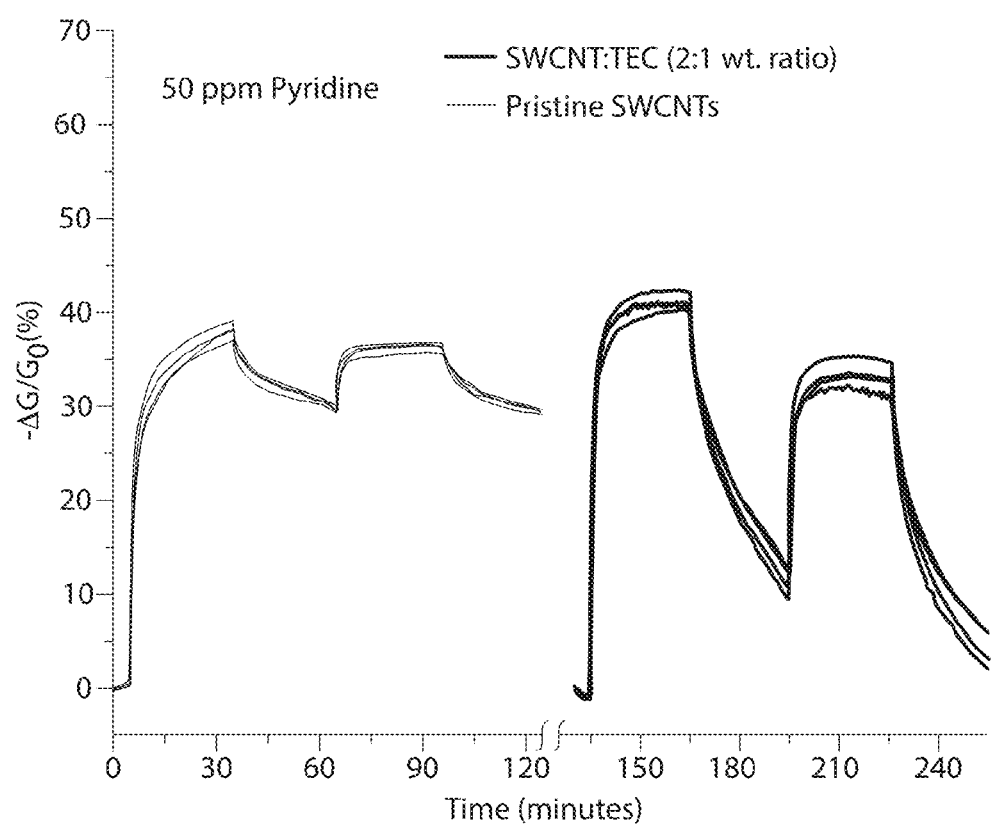
FIG. 23 shows the sensing responses ($-\Delta G/G_0$, %) of PENCILs deposited onto the surface of weighing paper between gold electrodes by mechanical abrasion to pyridine vapor.

To investigate the dynamic sensing range of the substrates, devices were exposed to various concentrations of pyridine (1-550 ppm) for five consecutive cycles of 30 s exposures with 60 s recovery times (FIG. 2B-C). The first exposure to pyridine was excluded from the device's average normalized conductance response as a result of its irreversibility and large variability (~10% coefficient-of-variance at 50 ppm pyridine on weighing paper). The sensors from each substrate successfully detected pyridine at its permissible exposure limit (1 ppm: American Conference of Governmental Industrial Hygienists [ACGIH]) and discriminated it from higher values (e.g., 20 ppm) (FIG. 22). Five of the six substrates examined demonstrated a similar magnitude (at 50 ppm pyridine: $\Delta G/G_0$=5.2-8.3%) of the conductive response towards pyridine. The sixth substrate, glass, was characterized by the poorest sensing performance (at least 2 times lower) across the range of concentrations examined.

Profilometry was used to investigate the surface morphology of the six substrates. The root-mean-square (RMS) surface roughness of weighing paper (RMS=2.5±0.7 µm), alumina (RMS=1.1±0.3 µm), adhesive tape (RMS=1.7±0.7 µm), unpolished side of the undoped silicon wafer (RMS=1.2±0.1 µm), PMMA (RMS=0.05±0.02 µm), and glass (RMS=5.9±0.5 nm) was determined. Surface roughness was measured using a stylus profiler with a stylus radius of 2.5 µm over a distance of 1400 µm with duration of scan of 30 s and applied force corresponding to a mass of 1 mg. The average measurement of surface roughness and the standard deviation were calculated from four scans over different regions between four gold electrode gaps of the same substrate.

Figure 9A:
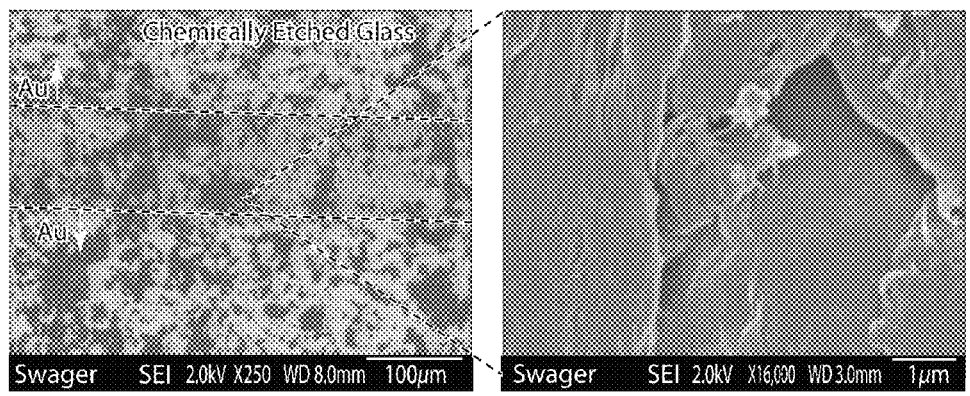
FIGS. 9A-9C shows high resolution Scanning Electron Microscopy (SEM) images of compressed pristine SWCNTs deposited by abrasion between and on top of gold electrodes onto (FIG. 9A) chemically etched glass, (FIG. 9B) laser etched glass, and (FIG. 9C) laser etched PMMA.
Figure 9B:
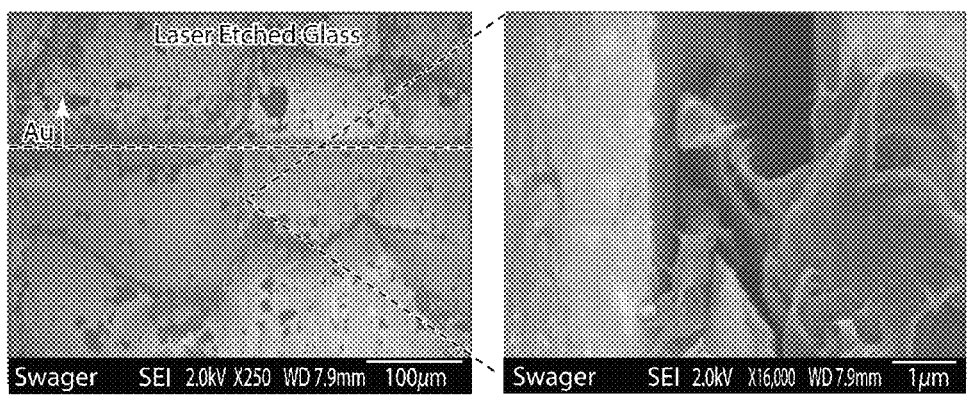
Figure 9C:
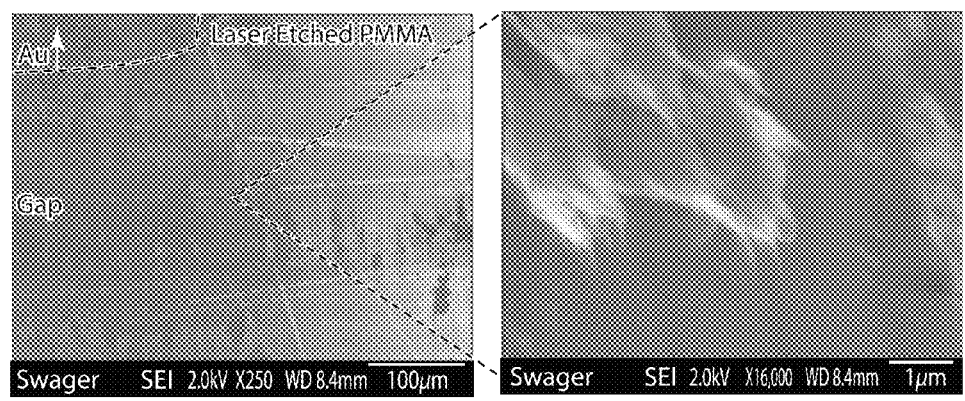
Figure 10:
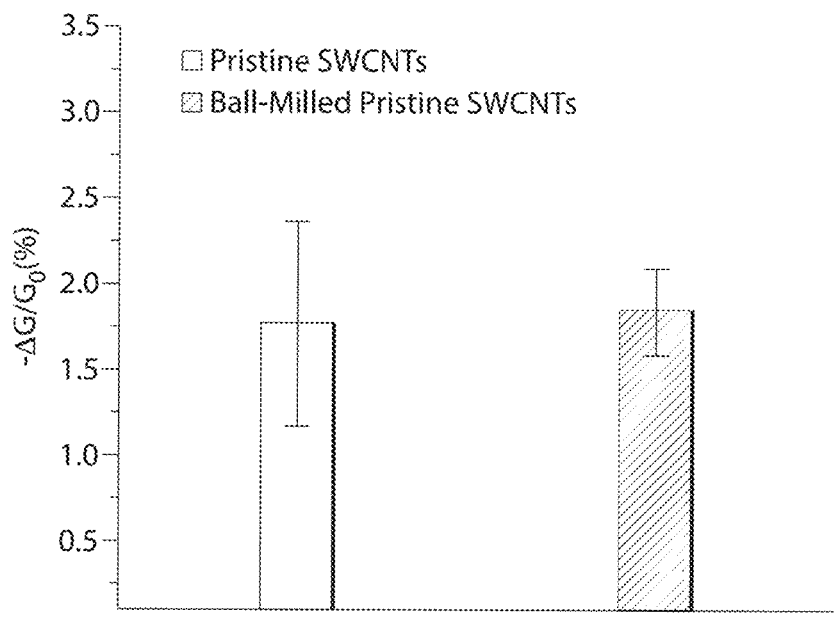
FIG. 10 shows the effect of ball milling of SWCNTs on the normalized average conductive responses of three pristine SWCNT-based sensors on weighing paper with gold electrodes simultaneously exposed four consecutive times to 50 ppm pyridine (first exposure exempt) for 30 s with recovery time of 60 s.
Figure 11:
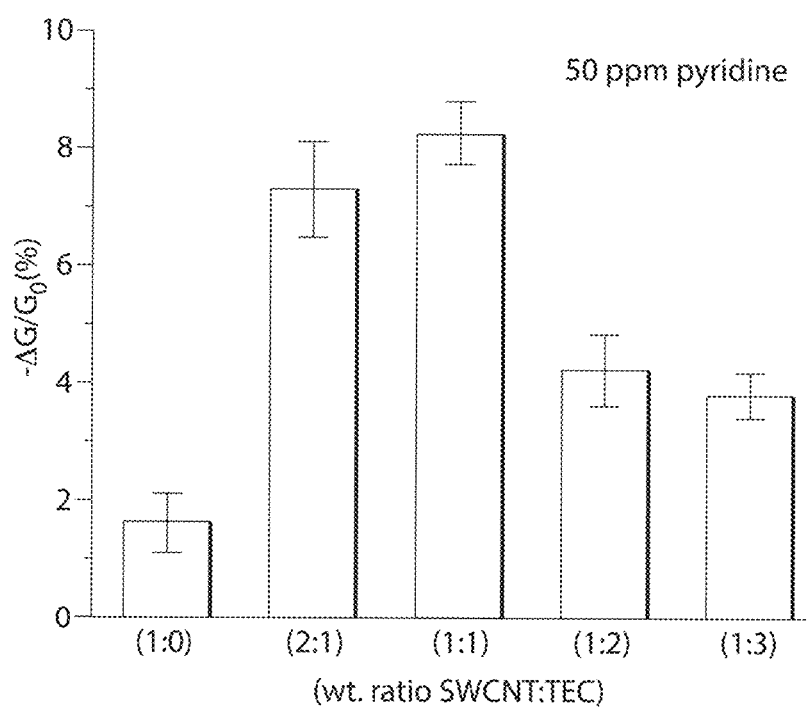
FIG. 11 shows the effect of mixing SWCNT and TEC at different mass ratios on the normalized average conductive responses of two sensors with SWCNT:TEC deposited between and on top of gold electrodes onto weighing paper (0.3 mm gap size) simultaneously exposed four consecutive times to 50 ppm pyridine (first exposure exempt) for 30 s with a recovery time of 60 s.

In order to facilitate the deposition of PENCILs by abrasion on relatively smoother surfaces, substrates (PMMA and glass) were modified by laser or chemical etching, as described herein. However, the laser-etched glass did not facilitate improved deposition of materials by DRAFT as a result of surface artifacts and cracks on the surface of the glass that we introduced by the etching process (FIG. 9).

Example 3

This example describes the fabrication and characterization of graphite electrodes by mechanical abrasion.

Figure 17:
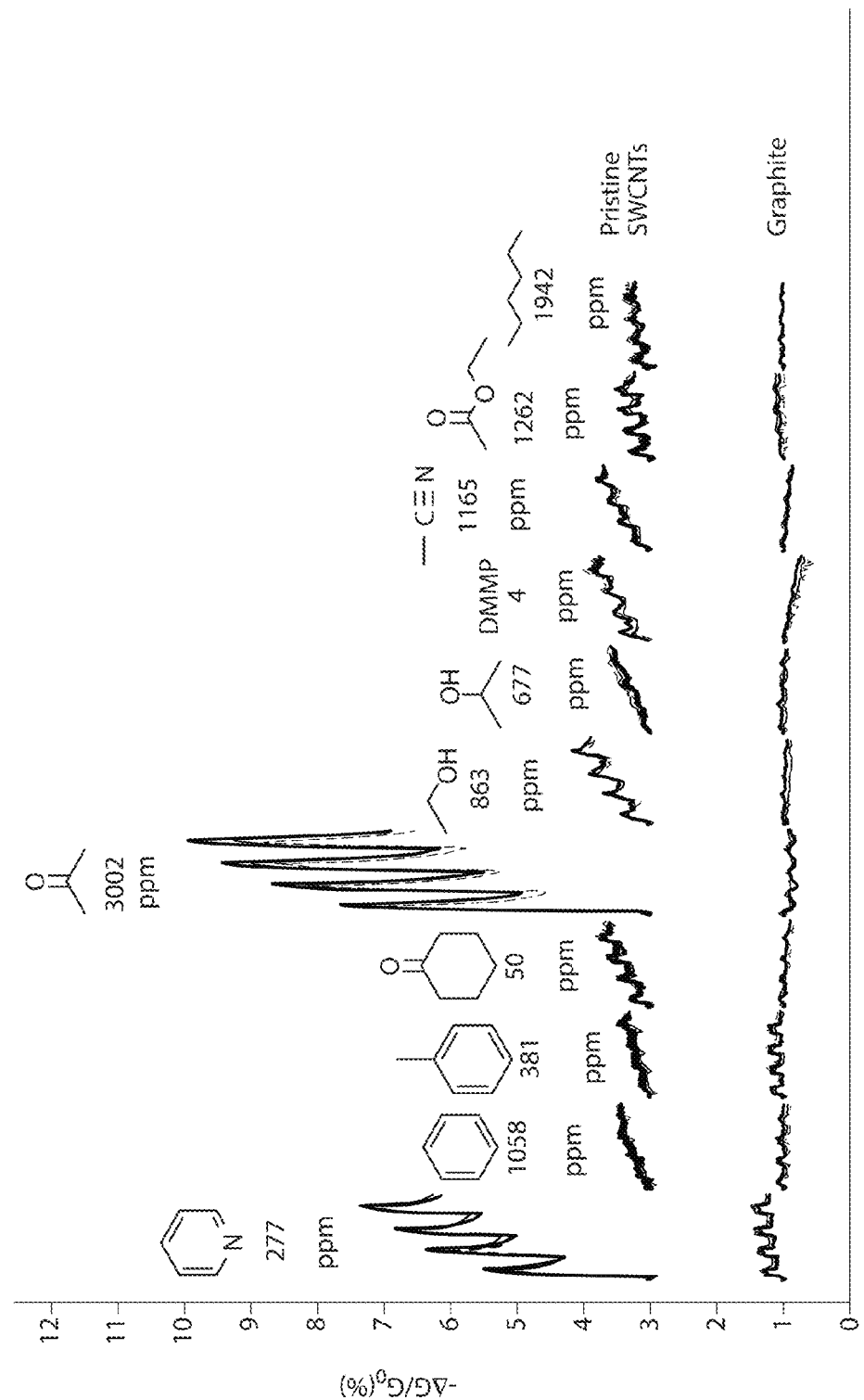
FIG. 17 shows the sensing responses ($-\Delta G/G_0$, %) from graphite and pristine SWCNTs deposited on the surface of weighing paper between gold electrodes.

The response of pristine SWCNTs to the response of a commercial 9B graphite pencil when both were abraded between gold electrodes on the surface of weighing paper (3 sensors each) and exposed to various analytes was explored. The resistive range of the sensors was 1-2 kΩ The sensing response of graphite was 5 times smaller in response to 277 ppm pyridine than the response of pristine SWCNTs (FIG. 17). This study suggested that SWCNTs are generally more sensitive materials than graphite towards a wide range of chemical analytes, a difference that may be amplified further when the sheet resistance of graphite electrodes within a chemiresistor architecture is substantially lower than that of SWCNT-based sensing materials.

Example 4

This example describes the fabrication and characterization of fully-drawn chemical sensors by mechanical abrasion.

Figure 19:
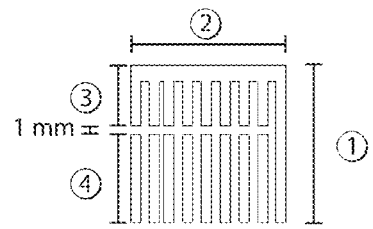
FIG. 19 shows the resistive measurements of carbon-based electrodes used for chemiresitive sensors on various substrates.
Figure 20:
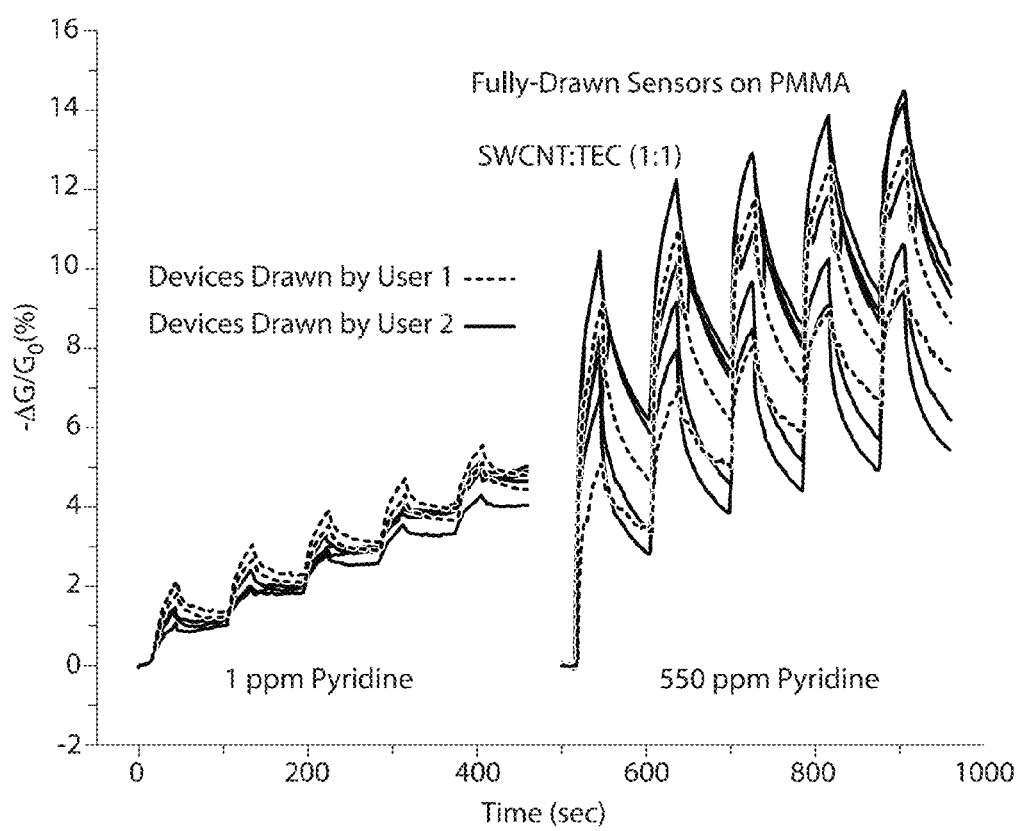
FIG. 20 shows user-to-user reproducibility for fully-drawn carbon-based chemiresistors.
Figure 21:
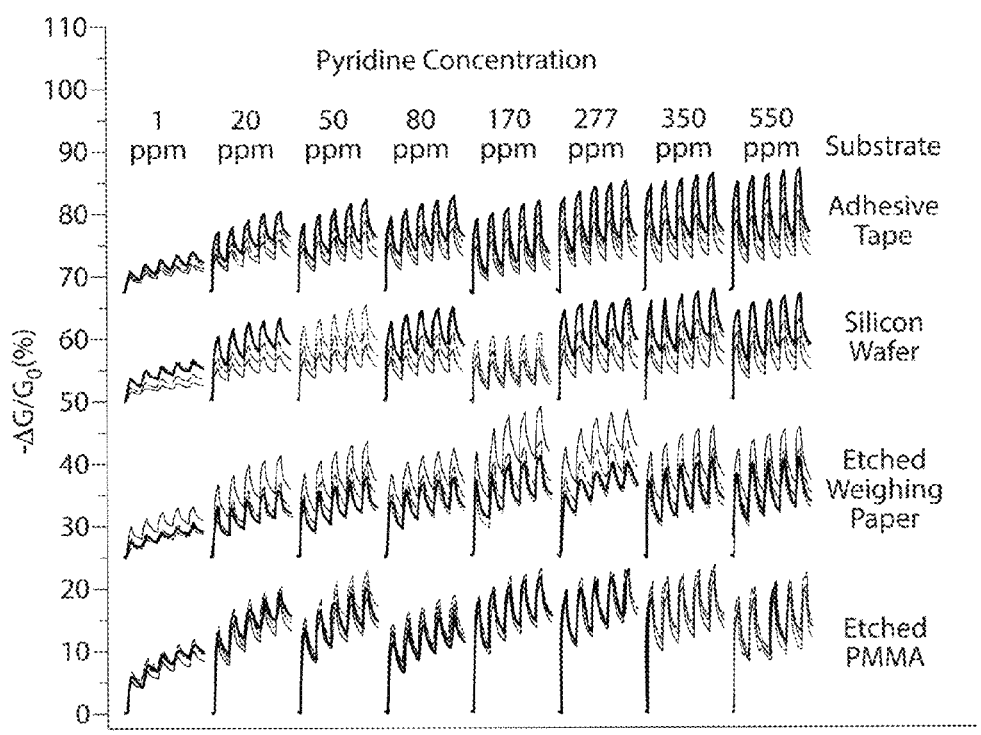
FIG. 21 shows the sensing responses ($-\Delta G/G_0$, %) of four fully-drawn devices on various substrates.

The substrates were cleaned as described above. PENCILs were inserted into a holder and deposited by DRAFT onto a substrate to generate a conductive line approximately 3 mm in length until about 400 to about 600 kΩ resistance range was achieved. Carbon-based electrodes with 1 mm gap size were deposited on top of the SWCNTs composites by abrasion using a graphite pencil. A stainless steel mask protected approximately 1 mm of the sensing material from contamination by graphite. The graphitic layers were deposited until a certain range of sheet resistance was obtained, as summarized in FIG. 19.

Fully-drawn sensors have the advantage of being easily fabricated on-demand or replaced. The fabrication and characterization of sensing performance of fully-drawn chemical sensors on four different substrates was performed (FIG. 3). Generally, SWCNT:TEC (1:2 wt. ratio) was deposited by DRAFT and carbon-based electrodes deposited by mechanical abrasion and partially-drawn sensors (SWCNT:TEC (1:2 wt. ratio)) were deposited by DRAFT and gold electrodes were deposited by thermal evaporation. The two-step fabrication process to generate fully-drawn working devices was performed (FIG. 3A-B) on the unmodified surface of adhesive tape and an unpolished undoped highly resistive (resistance>10000 Ω-cm) silicon wafer. The first step involved drawing a line of sensing material (SWCNT:TEC) approximately 3 mm in length having a resistance of about 400 to about 600 kΩ. The second step generated carbon-based electrodes by abrasion of a graphite pencil on top of the sensing material leaving a 1 mm gap between the electrodes. A stainless steel mask was used as a stencil to guide the deposition of graphite-based electrodes and to protect 1 mm of the CNT-based sensing material from contamination by graphite.

FIG. 3 show the average normalized conductive response (first exposure exempt) of at least four fully-drawn sensors (black squares) and partially drawn sensors (white triangles) simultaneously exposed to various concentrations of pyridine for 30 s with 60 s recovery time.

Figure 3A:
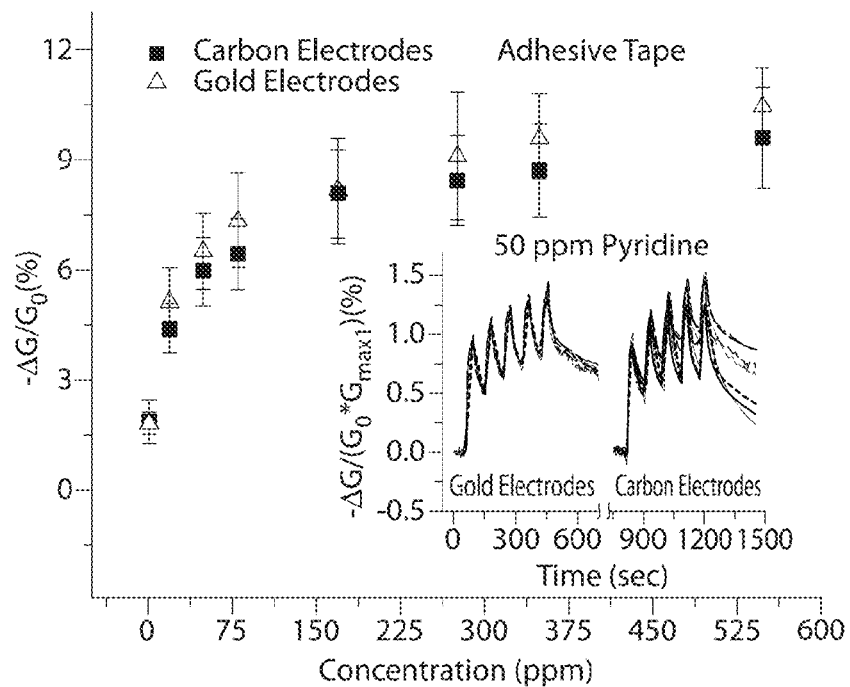
FIGS. 3A-3D shows the response of various devices comprising SWNCT:TEC deposited by abrasion between graphite electrodes deposited by abrasion or gold electrodes deposited by thermal evaporation, including the average normalized conductance over time for sensors drawn on (FIG. 3A) a substrate comprising adhesive tape, (FIG. 3B) a substrate comprising a silicon wafer, (FIG. 3C) a substrate comprising weighing paper, and (FIG. 3D) a substrate comprising PMMA.
Figure 3B:
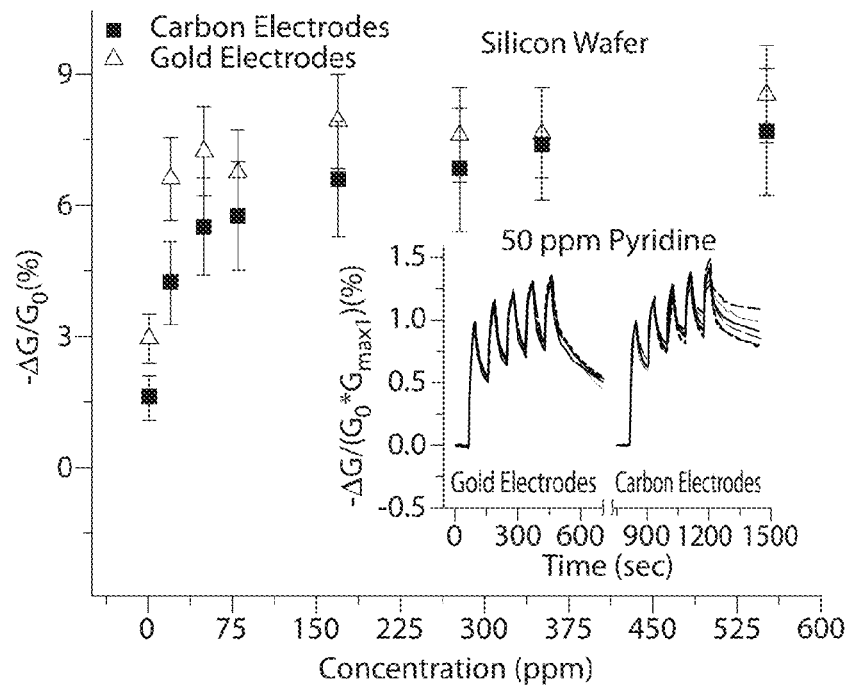
Figure 3C:
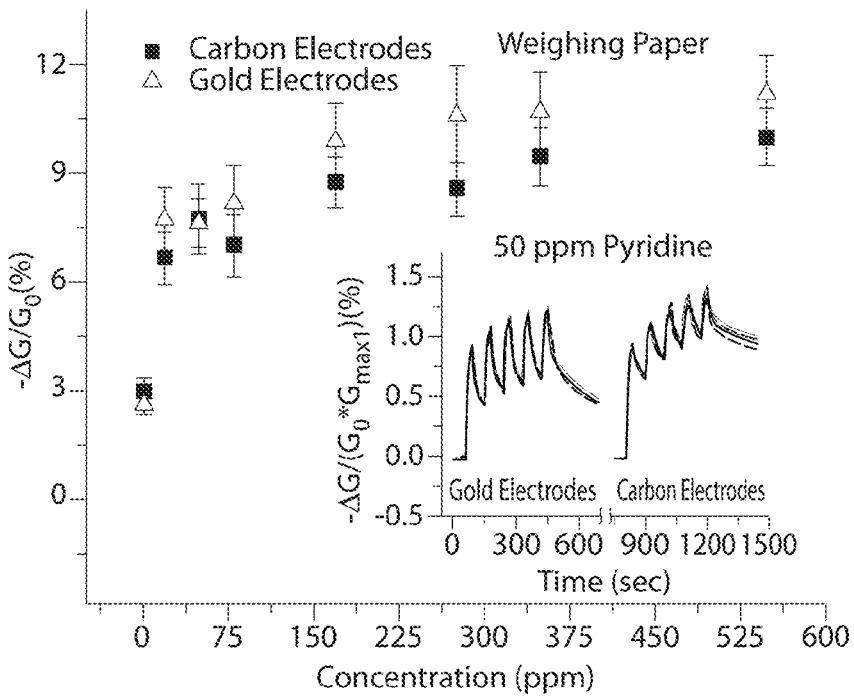
Figure 3D:
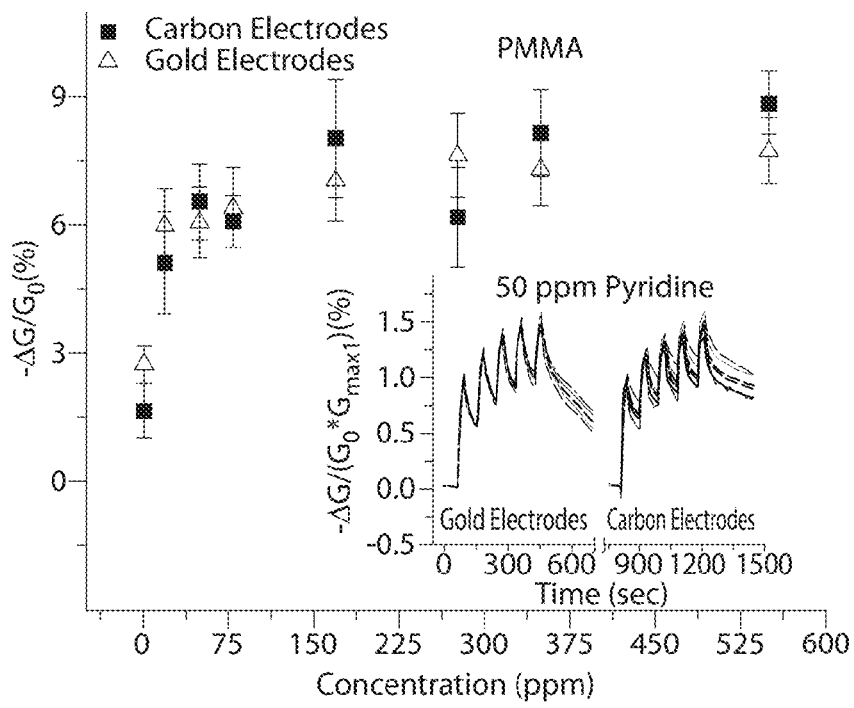
Figure 18:
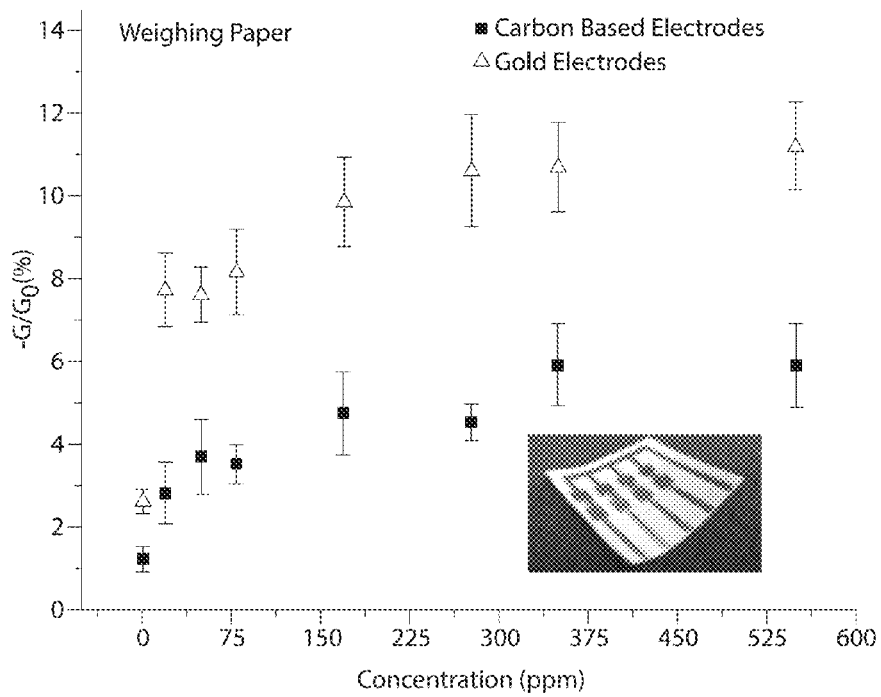
FIG. 18 shows the sensing responses ($-\Delta G/G_0$, %) of at least four devices fabricated by depositing SWCNT:TEC (2:1 mass ratio) between carbon-based electrodes or gold electrodes by abrasion onto weighing paper simultaneously exposed five consecutive times to various concentrations of pyridine for 30 s with recovery time of 60 s.

Graphite does not generally abrade efficiently on smooth surfaces (e.g., weighing paper and PMMA) and yielded electrodes with higher sheet resistance (FIG. 18). This limitation was overcome by introducing an additional step into the fabrication procedure by increasing surface roughness of the substrate through chemical or laser etching. This additional step had an added advantage of localizing the abrasion of graphite into predefined regions on the chip. Using this strategy, the ability to precisely fabricate fully-drawn working devices on laser-etched surfaces of weighing paper and PMMA was demonstrated (FIG. 3C-D).

Example 5

This example describes the use of devices fabricated using methods described herein in sensing pyridine.

The average normalized conductive response of the fabricated chemiresistors with carbon-based electrodes is comparable to the standard gold electrode upon exposures to several concentrations of pyridine on various substrates. FIG. 3 shows the average normalized conductive responses (first exposure exempt) of at least four devices with either gold electrodes or carbon-based electrodes simultaneously exposed five consecutive times to various concentrations of pyridine for 30 s with 60 s recovery times. The inset displays the normalized conductance trace (additionally normalized to the first exposure) over time of seven devices with either gold electrodes or carbon-based electrodes simultaneously exposed five consecutive times to 50 ppm pyridine for 30 s with 60 s recovery time. Device-to-device variation was investigated between fully-drawn and partially-drawn sensors on 4 substrates (weighing paper, PMMA, silicon, and adhesive tape) using SWCNT:TEC as sensing material and graphite or gold as electrodes. At least 7 devices were exposed 5 consecutive times to 50 ppm pyridine 30 s with 60 s recovery times. The fully-drawn sensors yielded slightly higher (1-5%) coefficient-of-variance in response to pyridine compared to the partially drawn sensors (weighing paper: fully-drawn sensor [12%] and partially-drawn sensor [9%]) excluding the first exposure to pyridine).

Example 6

This example describes the fabrication and characterization of fully-drawn sensing arrays.

The fabrication of fully-drawn chemical sensors was extended to chemical sensing arrays. Different sensing materials were generated by mechanical mixing of SWCNTs with a solid selector, two different ionic liquids, or a plasticizer to draw a SWCNT-based chemiresistive array (FIG. 4). The chemical structures of the selectors used are shown in FIG. 4A. Selector 1L was used for pyridine sensing. Selector 2L and 3L are ionic liquids that have been previously used in conjunction with graphene and a quartz crystal microbalance to detect benzene. Selector 1S is a solid selector with a functional group handle (hexafluoroisopropanol) that has been previously used to detect Dimethyl methylphosphonate (DMMP) vapor via hydrogen-bond acids. These selector: SWCNT composites were abrasion deposited over an etched pattern on the weighing paper. Graphite was then abraded on top of the etched pattern on the weighing paper leaving gap size of 1 mm between the electrodes. The chemiresistive array was then exposed to a variety of gas analytes that can be classified as biomarkers, nerve agents, industrial hazards, quality of food markers, and gasoline. To investigate the selectivity of the devices that were fully-drawn and placed into array, the devices were exposed five consecutive times to various analytes for 30 s with a 60 s recovery time. The color scale mapping of the average normalized change of conductance (first exposure exempt) of fully-drawn devices is shown in FIG. 4B. Each selector had enhancements in sensitivity and selectivity towards certain analytes compared to pristine SWCNTs. Selector 1S caused the SWCNTs to be more sensitive towards DMMP (1.3 times higher sensitivity). This may be due to the hexafluoroisopropanol group engaging in intermolecular hydrogen bonding with the aniline moiety thereby reducing the binding of DMMP. The ionic liquid selectors 2L and 3L did not show enhancements towards benzene possibly due to the change in morphology from graphene (flat) to carbon nanotubes (cylindrical) or change in sensing method from monitoring mass change (quartz crystal microbalance) to current change (chemiresistor). However, 2L and 3L did provide high selectivity towards amines and low sensitivity towards other analytes. The lone pair of electrons from the amines can interact with the ionic liquid to possibly cause charge separation thus enhancing the SWCNTs sensitivity and selectivity. Selector 1L displayed the highest sensitivity towards pyridine. The average normalized conductive response (first exposure exempted) of the fully-drawn CNT-based chemiresistive array towards various analytes was analyzed using Principle Component Analysis (PCA) (FIG. 4C). The four-component array successfully discriminated nitrogen-containing compounds from one another (pyridine, aniline, and triethylamine) and from other VOCs at low ppm concentration levels. Aniline and triethylamine are additional amines that are of interest since aniline has been reported as a possible biomarker for patients with lung cancer and triethylamine has been reported as a possible biomarker for patients with renal failure.

Abrasion over pre-patterned substrates successfully increased throughput, precision, and surface compatibility of DRAFT. Etching substrates (e.g., laser or chemical) enhanced the ability to control the location and other structural aspects of conductive carbon structures deposited on a variety of surfaces using DRAFT. This general strategy enabled the fabrication of fully-drawn chemiresistors on weighing paper, PMMA, adhesive tape, and an undoped silicon wafer by mechanical abrasion. Fully-drawn arrays on weighing paper were capable of detecting and discriminating low ppm concentrations of N-containing vapors (pyridine, aniline, and triethylamine). This fabrication methodology did not require specialized facilities (e.g., clean room, thermal evaporator) and was performed entirely on a desktop (with appropriate ventilation and safety precautions for handling nanomaterials). The method can be expanded to the fabrication of functional sensors, circuits, and tags by drawing on a variety of surfaces. This method can also be used towards a more efficient and rapid parallel fabrication of multiple devices by abrading surfaces of carbon materials against pre-patterned substrates.

Taken together, these examples demonstrate the production of functional chemiresistors, electrochemical sensors, strain and pressure sensors, and simple electrodes from commercially available starting materials within minutes.

What is claimed:

1. A method for fabricating a device, comprising:
providing a substrate having a surface comprising a first portion and a second portion;
contacting essentially identically the first portion and the second portion of the surface of the substrate with an article comprising a first material via mechanical abrasion, thereby forming the first material on the first portion while leaving the second portion essentially free of the first material, or forming the first material on the second portion in an amount at least 10% less per unit area of surface of the substrate than the first material formed on the first portion.

2. A method as in claim 1, wherein the first material comprises a carbon-based material.

3. A method as in claim 1, wherein the first material comprises a conductive material.

4. A method as in claim 1, wherein the first material comprises a semiconductive material.

5. A method as in claim 1, wherein the first material comprises an insulating material.

6. A method as in claim 1, wherein the first portion has a first average roughness and the second portion has a second average roughness, wherein the second average roughness is at least 10% less than the first average roughness.

7. A method as in claim 1, wherein an average affinity of the first portion to the first material is greater than an average affinity of the second portion to the first material.

8. A method as in claim 1, wherein the first material formed on the first portion has a first average thickness and the first material formed on the second portion has a second average thickness; wherein the second average thickness is at least 10% less than the first average thickness.

9. A method as in claim 1, wherein the method further comprises contacting the surface of the substrate with an article comprising a second material via mechanical abrasion, thereby forming the second material on the first material.

10. A method as in claim 9, wherein the second material comprises a carbon based material.

11. A method as in claim 1, wherein the method comprises modifying the surface of the substrate to form a third portion, contacting the third portion with the article comprising a second material via mechanical abrasion, thereby forming the second material on the third portion while leaving the first portion and/or second portion essentially free of the second material, or forming the second material on the third portion in an amount at least 10% less per unit area of surface of the substrate than the second material formed on the first portion and/or second portion.

12. A method as in claim 1, wherein modifying the surface of the substrate comprises patterning, chemically etching, scratching, chemically modifying, and/or nanoindenting the surface of the substrate.

13. A method as in claim 1, wherein the method further comprises providing an electrode material in electrochemical communication with the first material.

14. A method as in claim 1, wherein the method further comprises forming an electrical circuit comprising the conductive material.

15. A method as in claim 1, wherein the method forms a device that has an electrical resistance that varies with the direction of electrical current.

16. A method as in claim 1, wherein the conductive material comprises nanostructures, polymers, small molecules, metal-containing species, biological species, or combinations thereof.

17. A method as in claim 1, wherein the conductive material comprises carbon nanotubes, graphene, carbon powder, polymers, small molecules, metal salts/nanoparticles, powders, proteins, DNA, or combinations thereof.

18. A method as in claim 1, wherein the carbon-based material is a nanotube or graphite.

19. A method as in claim 1, wherein the substrate or patterned substrate comprises paper, fabric, a polymer, glass, metal, diamond, nails or skin.

20. A method as in claim 1, wherein the substrate or patterned substrate is formed via chemical etching, scratching, chemical modification, and/or nanoindentation.

21. A method for fabricating a device, comprising:
providing a substrate having a surface comprising a first portion and a second portion, wherein an average affinity of the first portion to a first material is greater than an average affinity of the second portion to the first material;
contacting the first portion and the second portion of the surface of the substrate essentially identically with an article comprising the first material via mechanical abrasion.

\* \* \* \* \*